US012667309B2

(12) United States Patent
Kim et al.

(10) Patent No.: US 12,667,309 B2
(45) Date of Patent: Jun. 30, 2026

(54) WEARABLE ELECTRONIC DEVICE INCLUDING BIOMETRIC SENSOR AND WIRELESS CHARGING MODULE

(71) Applicant: SAMSUNG ELECTRONICS CO., LTD., Suwon-si (KR)

(72) Inventors: Hongki Kim, Suwon-si (KR); Youngjin Oh, Suwon-si (KR); Seungho Lee, Suwon-si (KR); Jungsoo Kim, Suwon-si (KR); Ikhyun Cho, Suwon-si (KR); Chijeong Choi, Suwon-si (KR); Seungnyun Kim, Suwon-si (KR); Yongsang Yun, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1200 days.

(21) Appl. No.: 16/844,432

(22) Filed: Apr. 9, 2020

(65) Prior Publication Data

US 2020/0323489 A1      Oct. 15, 2020

(30) Foreign Application Priority Data

Apr. 12, 2019    (KR) ........................ 10-2019-0043294

(51) Int. Cl.
*A61B 5/00*       (2006.01)
*A61B 5/1455*   (2006.01)
(Continued)

(52) U.S. Cl.
CPC ............ *A61B 5/681* (2013.01); *A61B 5/0059* (2013.01); *A61B 5/1455* (2013.01); *G06F 1/163* (2013.01);
(Continued)

(58) Field of Classification Search
CPC ..... A61B 5/681; A61B 5/1455; A61B 5/0261; A61B 2562/166; H05K 2201/10151
See application file for complete search history.

(56) References Cited

U.S. PATENT DOCUMENTS 10,485,478 B1 * 11/2019 Mirov ...................... A61B 5/01
2014/0017998 A1    1/2014 Kim et al.
(Continued)

FOREIGN PATENT DOCUMENTS

CN            107041739        8/2017
EP              3012911        4/2016
(Continued)

OTHER PUBLICATIONS

International Search Report and Written Opinion dated Jul. 17, 2020 in counterpart International Application No. PCT/KR2020/004887.
(Continued)

*Primary Examiner* — Linda C Dvorak
*Assistant Examiner* — Christine A Dedoulis
(74) *Attorney, Agent, or Firm* — Nixon & Vanderhye, P.C.

(57)                ABSTRACT

Various embodiments relate to an electronic device including a biometric sensor and a wireless charging module. According to various embodiments, there may be provided a sensor module including: a circuit board; a biometric sensor disposed in a first area of a first surface of the circuit board; a conductive line disposed in a second area of the first surface of the circuit board and surrounding at least a portion of the biometric sensor when viewed from above the first surface of the circuit board; a plurality of electrode pads disposed in a third area of a second surface of the circuit board; and at least one electronic component comprising electronic circuitry disposed in the third area of the second
(Continued)

surface of the circuit board and electrically connected to at least one of the plurality of electrode pads.

18 Claims, 13 Drawing Sheets

(51) Int. Cl.

| | | |
|---|---|---|
| *G06F 1/16* | (2006.01) |
| *H02J 50/10* | (2016.01) |
| *H05K 1/02* | (2006.01) |
| *H05K 1/11* | (2006.01) |
| *H01R 12/51* | (2011.01) |
| *H01R 13/6594* | (2011.01) |

(52) U.S. Cl.
CPC ............ *H02J 50/10* (2016.02); *H05K 1/0218* (2013.01); *H05K 1/111* (2013.01); *A61B 2560/0214* (2013.01); *A61B 2562/166* (2013.01); *H01R 12/51* (2013.01); *H01R 13/6594* (2013.01); *H05K 1/0298* (2013.01); *H05K 2201/09472* (2013.01); *H05K 2201/10151* (2013.01)

(56) References Cited

U.S. PATENT DOCUMENTS

| | | | |
|---|---|---|---|
| 2014/0094674 A1 | 4/2014 | Nurmikko et al. |
| 2015/0366479 A1* | 12/2015 | Kim ..................... A61B 5/1126 |
| | | | 345/156 |
| 2016/0268848 A1 | 9/2016 | Nalbant |

| | | | |
|---|---|---|---|
| 2016/0338646 A1 | 11/2016 | Lee et al. |
| 2017/0194809 A1 | 7/2017 | Partovi et al. |
| 2017/0224236 A1 | 8/2017 | Ho et al. |
| 2017/0296088 A1* | 10/2017 | Choi ..................... A61B 5/7271 |
| 2018/0039233 A1 | 2/2018 | Shim et al. |
| 2018/0090826 A1 | 3/2018 | De Costa Bras Lima et al. |
| 2018/0116532 A1* | 5/2018 | Han ......................... G06F 1/163 |
| 2018/0132738 A1* | 5/2018 | Choi ................. H01M 10/0436 |
| 2018/0165566 A1 | 6/2018 | Rogers et al. |
| 2019/0348209 A1* | 11/2019 | Wen ......................... H04B 5/26 |

FOREIGN PATENT DOCUMENTS

| | | |
|---|---|---|
| KR | 10-2014-0010245 | 1/2014 |
| KR | 10-2016-0127641 | 11/2016 |
| KR | 10-2016-0003458 | 10/2017 |
| KR | 10-2017-0118439 | 10/2017 |
| KR | 10-2018-0033468 | 4/2018 |
| KR | 10-2018-0042194 | 4/2018 |
| KR | 10-2018-0046762 | 5/2018 |
| WO | 2019/050157 | 3/2019 |

OTHER PUBLICATIONS

Extended Search Report and Written Opinion dated Apr. 4, 2022 in counterpart European Application No. 20788284.6.
Office Action dated May 28, 2024 in Korean Patent Application No. 10-2019-0043294 and English-language translation.
Communication pursuant to Article 94(3) EPC dated Jun. 3, 2024 in European Patent Application No. 20788284.6.
Communication pursuant to Article 94(3)EPC dated Sep. 12, 2025 in European Patent Application No. 20788284.6.

* cited by examiner

WEARABLE ELECTRONIC DEVICE INCLUDING BIOMETRIC SENSOR AND WIRELESS CHARGING MODULE

CROSS-REFERENCE TO RELATED APPLICATION

This application is based on and claims priority under 35 U.S.C. § 119 to Korean Patent Application No. 10-2019-0043294, filed on Apr. 12, 2019, in the Korean Intellectual Property Office, the disclosure of which is incorporated by reference herein in its entirety.

BACKGROUND

Field

The disclosure relates to an electronic device including a biometric sensor and a wireless charging module.

Description of Related Art

The term "electronic device" may refer, for example, to a device that performs a specific function depending on a program incorporated therein, such as an electronic scheduler, a portable multimedia reproducer, a mobile communication terminal, a tablet PC, an image/sound device, a desktop PC, a laptop PC, or a vehicular navigation system, as well as a home appliance. The above-mentioned electronic devices may output, for example, information stored therein as a sound or an image. As the integration degree of electronic devices has increased and super-high speed and large-capacity wireless communication have become popular, various functions have recently been provided in a single electronic device, such as a mobile communication terminal. For example, various functions, such as an entertainment function (e.g., a game function), a multimedia function (e.g., a music/video reproducing function), a communication and security function for mobile banking, a schedule management function, and an e-wallet function, are integrated in a single electronic device, in addition to a communication function.

Portable electronic devices are generally equipped with a flat type display and a battery, and have a bar-type, folder-type, or sliding-type appearance. Recently, with the development of electronic communication technology, electronic devices have been miniaturized, and thus electronic devices, which are wearable on a portion of a human body, such as a wrist or a head, have become commercially available. Wearable electronic devices, which have the shape of a watch or glasses, are good in portability and have various functions integrated in the miniaturized bodies thereof like a mobile communication terminal, thereby satisfying needs of consumers.

A wearable electronic device may include one or more sensors for acquiring biometric information of a user in view of the fact that the wearable electronic device is point mounted on the user's body. For example, a wearable electronic device may include sensors that are capable of acquiring the user's electrocardiogram (ECG), respiration, electrocardiogram (EMG), electrooculogram (EOG), electroencephalography (EEG), blood glucose, oxygen saturation (SpO2), photoplethysmogram (PPG), or body temperature, and that have functions of acquiring various information other than the above-mentioned biometric information.

A wearable electronic device may include a battery and a charging module in order to supply power required for the operations of sensors for acquiring biometric information, a display and various other electronic components. The battery charging method may be classified into a wired charging method or a wireless charging method.

Among the battery charging methods of the electronic device, the wired charging method may be less convenient than the wireless charging method because the fastening of the charger and the electronic device is made through direct fitting of a fastening terminal such as a dedicated clip or a cable. Therefore, in recent years, wireless charging is more preferred than wired charging. However, in the wireless charging method, charging efficiency may be changed drastically depending on the positions of the coil of the transmission terminal and the coil of the reception terminal, and is poor in efficiency compared to the wired charging method.

In the design of a wearable electronic device having a limited component mounting space, it may be important to place various components in place. According to an embodiment, various components, such as a sensor module, a battery charging module, and a magnetic material, may be mounted adjacent to the rear plate of the wearable electronic device.

SUMMARY

Embodiments of the disclosure provide an electronic device for improving component mountability with respect to a limited component mounting space, for example, in a wearable electronic device including a circuit for charging a battery wirelessly and an optically based biometric sensor.

According to various example embodiments, a sensor module may include: a circuit board; a biometric sensor disposed in a first area of a first surface of the circuit board; a conductive line disposed in a second area of the circuit board and surrounding at least a portion of the biometric sensor when viewed from above the first surface of the circuit board; a plurality of electrode pads disposed in a third area of a second surface of the circuit board; and at least one electronic component comprising electronic circuitry disposed in the third area of the second surface of the circuit board and electrically connected to the plurality of electrode pads.

According to various example embodiments, an electronic device may include: a housing including a first surface oriented in a first direction, and a second surface oriented in a second direction opposite the first direction; a display disposed such that at least a portion thereof is viewable through the first surface to display information outwards; a main circuit board disposed in a space between the first surface and the second surface; a sensor module disposed to be exposed to at least a partial area of the second surface; and a battery disposed in a space between the first surface and the main circuit board. The sensor module may include: a circuit board having one surface facing the second surface of the housing and another surface facing a third surface of the housing; a biometric sensor disposed in a first area on the one surface of the circuit board; a conductive line configured to wirelessly charge the battery, the conductive line being disposed in a second area of the circuit board and surrounding at least a portion of the biometric sensor when viewed from above the one surface of the circuit board; a plurality of electrode pads disposed in a third area of another surface of the circuit board; and an electronic component comprising electronic circuitry disposed in the third area of the another surface of the circuit board and electrically connected to the plurality of electrode pads.

According to various example embodiments, since a biometric sensor capable of obtaining biometric information of a user and wireless charging conductor capable of wirelessly charging a battery included in an electronic device are integrated in a single circuit board, it is possible to improve the mounting efficiency of electronic components and to miniaturize the electronic device.

In addition, according to various example embodiments, using a rear surface of an electronic device, it is possible to provide a structure capable of acquiring biometric information of a user through a sensor module or to provide a structure capable of performing a wireless charging function.

Furthermore, according to various example embodiments, since a structure capable of effectively blocking noise that may be received from an external electronic component during wireless charging is provided, it is possible to provide a sensor module having high wireless charging efficiency.

BRIEF DESCRIPTION OF THE DRAWINGS

The above and other aspects, features, and advantages of certain embodiments of the present disclosure will be more apparent from the following detailed description, taken in conjunction with the accompanying drawings, in which.

DETAILED DESCRIPTION

Figure 1:
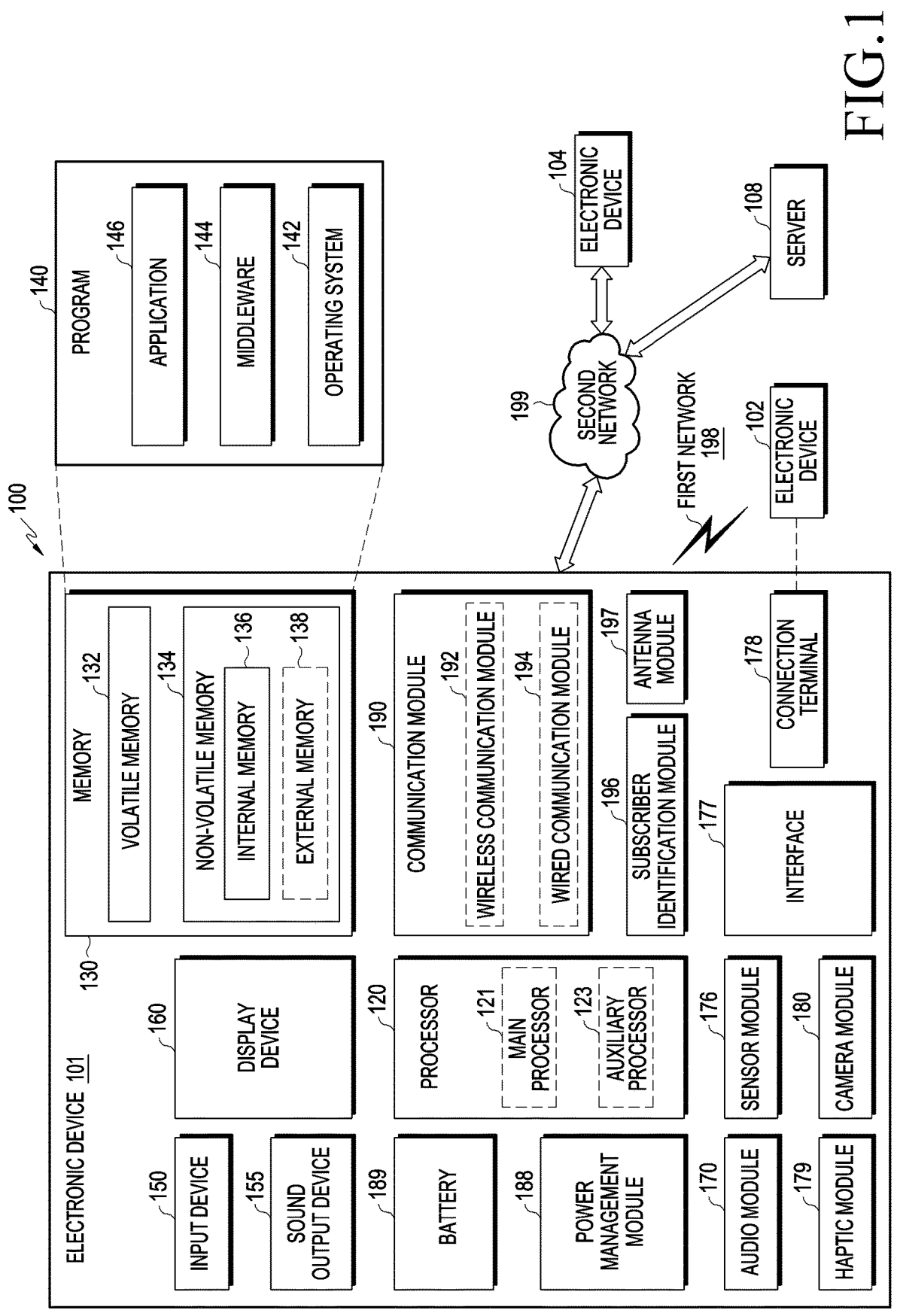
FIG. 1 is a block diagram illustrating an example electronic device in a network environment according to various embodiments.

FIG. 1 is a block diagram illustrating an example electronic device in a network environment according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an example embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless fidelity (WiFi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
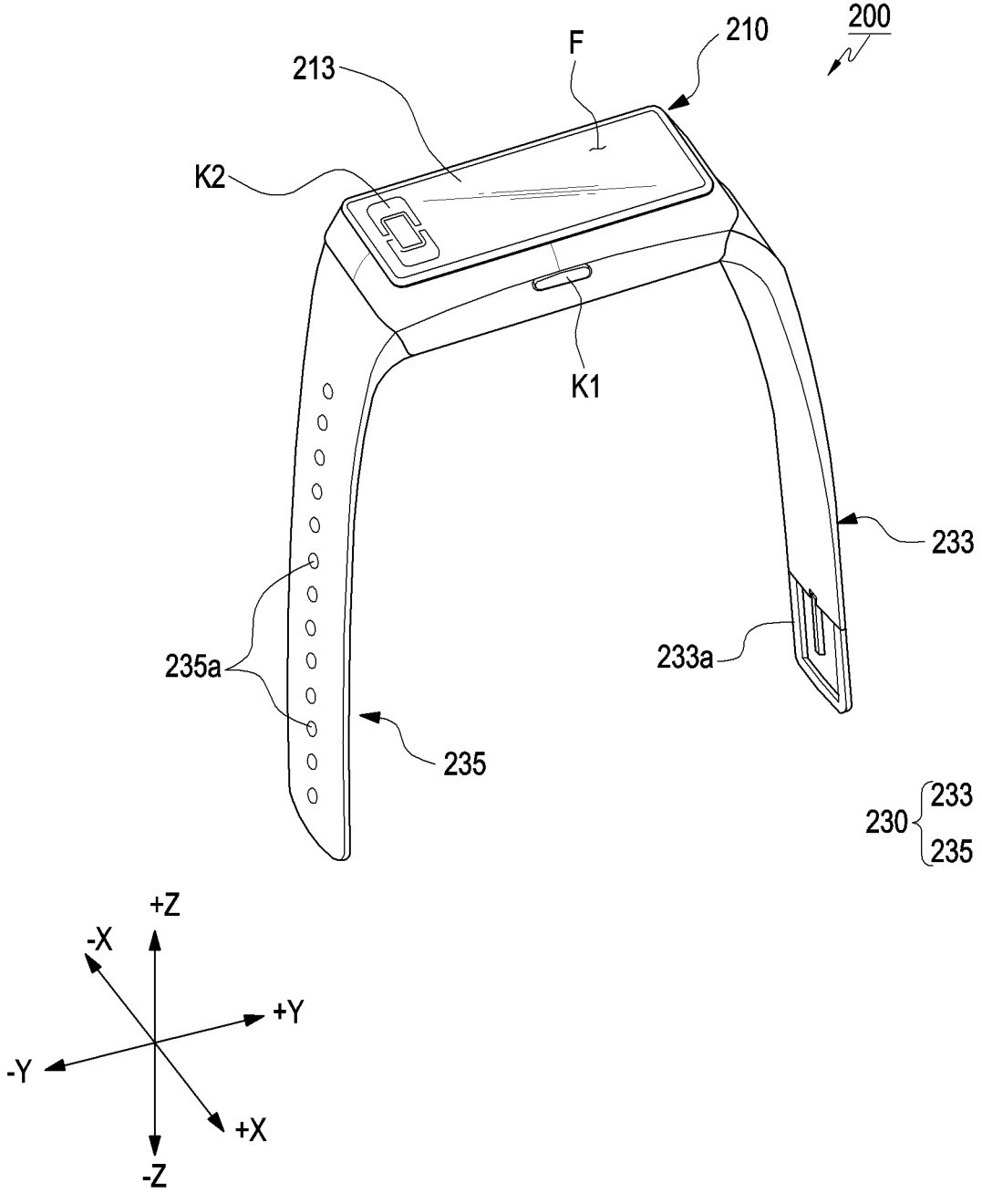
FIG. 2 is a perspective view illustrating an example electronic device according to various embodiments.

FIG. 2 is a perspective view illustrating an example electronic device 200 (e.g., the electronic device 101 in FIG. 1) according to various embodiments.

Referring to FIG. 2, an electronic device 200 according to various embodiments may include, for example, and without limitation, any of an ordinary analog watch, a digital watch, a smart watch, other wearable electronic devices such as a biometric signal measurement device, or the like, which may be worn around a user's wrist.

According to various embodiments of the disclosure, the electronic device 200 may include, for example, a body-wearable electronic device, for example, an electronic device that may be worn on a wrist, such as a watch, a bracelet, etc. However, various embodiments are not limited thereto, and the electronic device according to various embodiments may be implemented as various communication devices or auxiliary medical devices. In addition, the electronic device 200 according to various embodiments may be variously worn on a user's curved body portions. Examples of the user's curved body portions include, for example, and without limitation, a wrist, an arm, an ankle, etc. The electronic device 200 according to various embodiments may be conveniently worn on various portions of the user's body according to the configuration of the wearer.

According to various embodiments, the electronic device 200 may include a main body 210 (functional device unit) and a wearing unit 230 including wearing members (e.g., bands or straps). The main body 210 may include, for example, and without limitation, an analog watch module, a digital watch module, a display of a wearable electronic device, a module having various multi-functions, or the like, and may be a module for detecting a biometric signal or any of various modules for the user's movement. As another example, in a wearable electronic device, a touch panel may be incorporated in a display to be used as an input device. As another example, a biometric signal detection module may include a sensor for detecting the user's movement, a pad for measuring the user's heartbeat, or the like.

According to various embodiments, the main body 210 may have a bar-type shape. For example, the main body 210 may have a substantially rectangular shape extending in the longitudinal direction. However, the shape of the main body 210 is not limited to the rectangular shape, and the main body 210 may have various shapes in consideration of the user's preferences and/or arrangement of the internal components thereof. For example, the main body 210 may be manufactured to have a circular shape when viewed from above the main body.

According to various embodiments, in the main body 210, a display 213 for displaying various information (e.g., the display device 160 of FIG. 1), keys for inputting the various information (e.g., a side key K1 and a front key K2, and a sensor module 300 (see, e.g., FIG. 4) may be disposed. The main body 210 may have a front surface F oriented in a first direction (+Z) and a rear surface R (see, e.g., FIGS. 4 and 5) oriented in a second direction (−Z) and configured to come into contact with the user's body in a worn state. The display 213 may be disposed on the front surface F of the main body 210, and the sensor module 300 may be disposed on the rear surface R of the main body 210.

The wearing unit 230 may include an elastic material to enable the main body 210 to be stably worn on the user's body, and may bring the main body 210 into close contact with the user's body skin as needed. According to an embodiment, the wearing unit may be formed of various shape or materials (e.g., a rubber material, a plastic material, a metal, etc.).

According to various embodiments, the wearing unit 230 may include first and second wearing members 233 and 235. In addition, the wearing unit 230 may include means for fastening the first and second wearing members 233 and 235 to each other. For example, the first wearing member 233 may be provided with a first binding member 233a, and the second wearing member 235 may be provided with a plurality of binding holes 235a. The binding holes 235a may be arranged along the direction in which the second wearing member 235 extends, and may be engaged with the first binding member 233a. As the first binding member 233a is engaged with one of the binding holes 235a to bind the first and second wearing members 233 and 235 to each other, the wearing unit 230 may be maintained in a closed curve shape.

However, the binding structure described above is merely one of various embodiments, and may be replaced with other various structures (e.g., a protrusion-coupling-type binding structure) depending on the materials and structures of the first and second wearing members 233 and 235.

In the following description made with reference to the accompanying drawings including FIG. 2, in an orthogonal coordinate system of three axes, the "X axis" may correspond to the width direction of the main body 210 of the electronic device 210, the "Y-axis" may correspond to the length direction of the main body 210, and the "Z axis" may correspond to the thickness direction of the main body 210. In addition, in various embodiments, the "Z-axis direction" may be subdivided into a first (+Z) direction and a second (−Z) direction, the "Y-axis direction" may be subdivided into a third (+Y) direction and a fourth (−Y) direction, and the "X-axis" direction may be subdivided into a fifth (+X) direction and a sixth (−X) direction.

Figure 3:
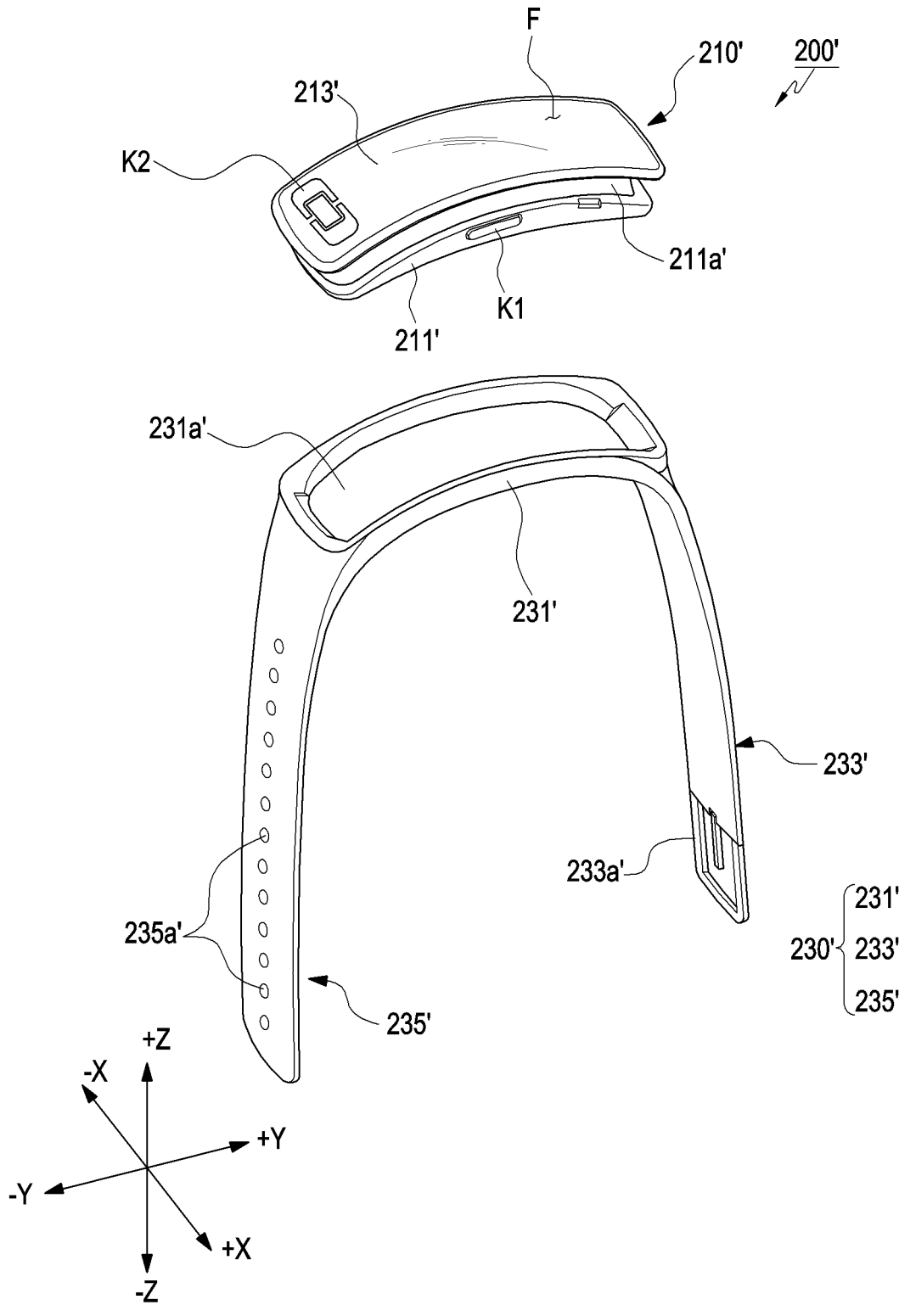
FIG. 3 is an exploded perspective view illustrating an example electronic device according various embodiments.

FIG. 3 is a perspective view illustrating an example electronic device 200' (e.g., the electronic device 101 in FIG. 1) according to various embodiments.

FIG. 3 illustrates an electronic device 200' that may be different in some respects from the electronic device 200 described above with reference to FIG. 2. Hereinafter, description will made with reference to portions different from those of the embodiment described with reference to FIG. 2, and redundant descriptions will not be repeated here.

According to various embodiments, a main body 210' may be configured to be attachable to/detachable from a wearing unit 230'. FIG. 3 illustrates the electronic device 200' according to various embodiments in the state in which the main body 210' is separated from the wearing unit 230'.

Referring to FIG. 3, since the main body 210' is configured to be attachable to/detachable from the wearing unit 230', the wearing unit 230' may be replaced with another one according to the user's personality or taste.

The wearing unit 230' may include first and second wearing members 233' and 235'. In addition, unlike the embodiment illustrated in FIG. 2, the wearing unit 230' may further include a portion (e.g., a seating portion 231') coupled with the main body 210'. The wearing unit 230' may further include an opening 231a' in which the main body 210' is detachably attached. Here, the seating portion 231' may be configured to be elastically deformable. In addition, the seating portion 231' may be formed to surround the circumference of the opening 231a'. When the main body 210' is coupled to the wearing unit 230', at least a portion of the seating portion 231' is fitted into a binding recess 211a' extending along the side surface of the main body 210'. Since the seating portion 231' includes an elastic material and elastically deformed, the seating portion 231' may be coupled while being deformed to match the shape of the housing 211', for example, the shape of the binding recess 211a'.

According to various embodiments, the body portion 210' of the electronic device 200' may have a curvature at least partially corresponding to that of the corresponding body portion of the user. According to an embodiment, the housing 211' forming the outer surface of the main body 210' may be formed to have a predetermined curvature. Correspondingly, the display 213' disposed on the front surface F of the main body 210' may also be formed to have the predetermined curvature.

Since the wearing unit 230' has a replaceable structure, the wearable unit 230' may be implemented in various designs or colors and may be replaced according to the user's taste.

For example, the wearing unit 230' may be used as an accessory that represents the user's own personality.

Figure 4:
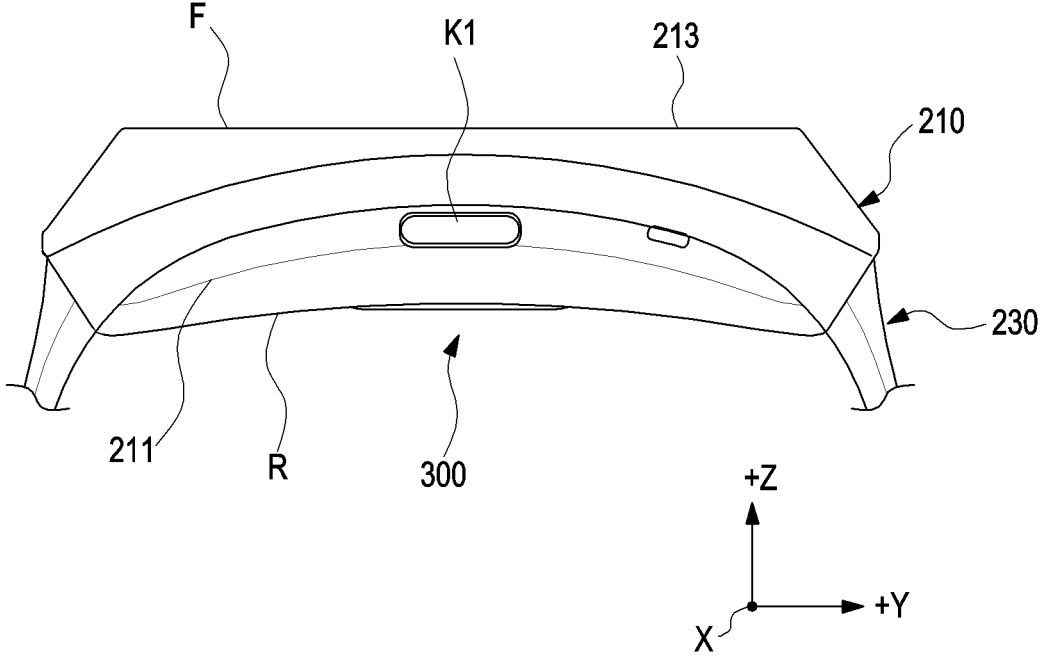
FIG. 4 is a side view illustrating a main body of an example electronic device according to various embodiments.

FIG. 4 is a side view illustrating the main body 210 of the example electronic device 200 according to various embodiments.

Referring to FIG. 4, a housing 211 includes a front surface F, a rear surface R, and a side surface connecting the front surface F and the rear surface R to each other, and the front surface F and/or the rear surface R may be configured to have a curvature. The front surface F of the housing 211 may be a surface on which the display device 213 is mounted, and the rear surface R of the housing 211 may be a wearing surface, which comes into contact with the corresponding body portion of the user. According to an embodiment, the front surface F may be flat as illustrated in FIG. 4 or may have a curvature as illustrated in FIG. 3. According to an embodiment, the rear surface R may have a curvature, which may be determined in consideration of, for example, and without limitation, a product design, wrist circumferences of various users, wearing sensation provided by the curvature, etc.

According to various embodiments, the housing 211 may have an appropriate curvature determined in consideration of the shape of the corresponding body portion of the user, for example, the thickness and curvature of the user's wrist, thereby improve the user's wearing sensation and compatibility to various consumer wrist circumferences.

According to various embodiments, the housing 211 may accommodate the display 213, the sensor module 300, a circuit board, a battery, and/or various electronic components. A portion of the housing 211, for example, the rear surface or the side surface of the housing 211, may at least partially include a material that is capable of transmitting a wireless signal or a magnetic field.

According to various embodiments, the front surface F of the housing 211 may be provided with the display 213, the rear surface R may be provided with a sensor module 300, for example, a biometric detection sensor, and the rear surface R may come into contact with the corresponding body portion of the user (e.g., a wrist).

According to various embodiments, the display 213 may include, for example, and without limitation, a liquid crystal display (LCD), a light-emitting diode (LED) display, an organic light-emitting diode (OLED) display, a microelectromechanical system (MEMS) display, an electronic paper display, or the like. According to various embodiments, the display 213 may have an antenna radiator mounted on the inner or outer surface thereof to perform a wireless communication function.

According to various embodiments, the display 213 provided in the main body 210 may be implemented as a flat display or a curved display having a predetermined curvature. According to various embodiments, the display 213 may further include a sensing unit that detects capacitance, pressure, temperature, etc. in response to the user's touch, for example, a touch panel. The touch panel may be integrated in the display 213.

Image information (e.g., a photograph or a video image) may be displayed to the outside of the electronic device 200 using the display 213, and an execution screen for various applications (e.g., a game, Internet banking, and schedule management) may be output according to the user's operation.

According to various embodiments, the sensor module 300 provided in the main body 210 may be disposed to be exposed to the rear surface R of the electronic device 200. For example, the biometric sensor module 300 may be configured to be in close contact with the rear surface R of the housing 211, which is to come into contact with the corresponding body portion of the user to detect information to be acquired (e.g., the user's vital reaction) at a position that is as close to the corresponding body portion as possible. For example, when the sensor module 300 includes a biometric sensor, at least one of, for example, and without limitation, the user's photoplethysmogram (PPG), sleep interval, skin temperature, heart rate, or the like, may be detected using the sensor module 300 provided on the rear surface R of the electronic device 200. The biometric sensor will be described in greater detail below with reference to FIG. 9.

Figure 5:
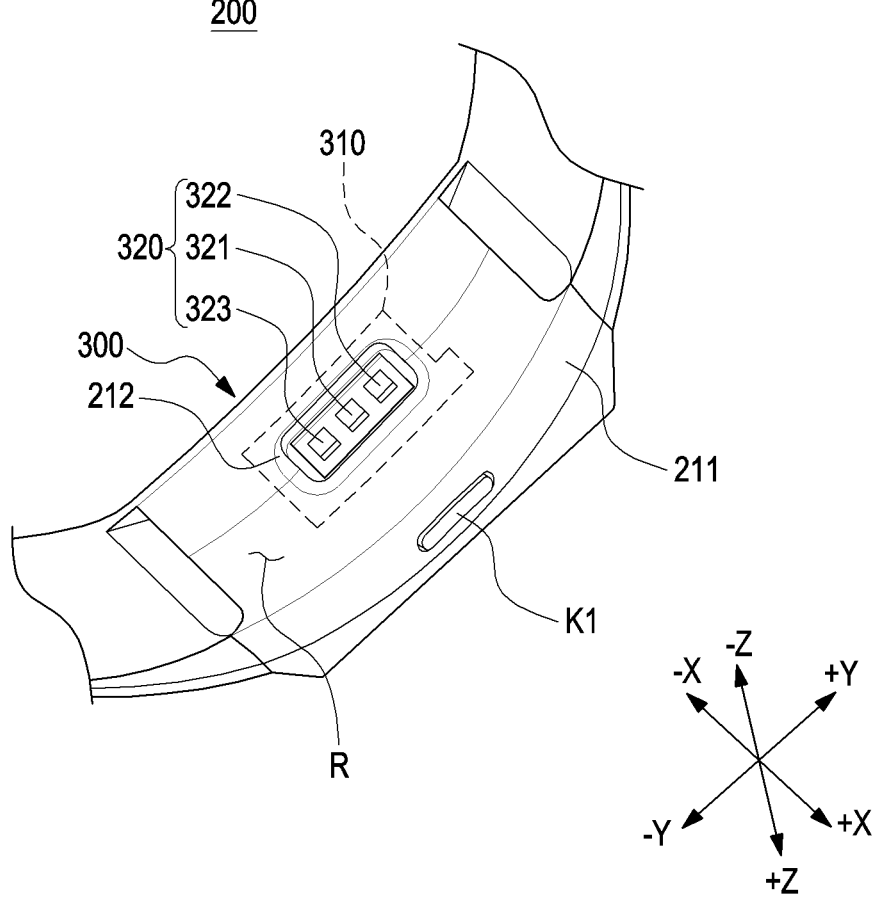
FIG. 5 is a rear perspective view illustrating a sensor module disposed on the rear side of an example electronic device according to various embodiments.

FIG. 5 is a rear perspective view illustrating the sensor module 300 disposed on the rear surface of the electronic device 200 according to various embodiments.

Referring to FIG. 5, the sensor module 300 may be disposed on the rear surface R of the housing 211. According to various embodiments, the sensor module 300 may be disposed on a circuit board 310 disposed inside the housing 211. At least a portion of the sensor module 300 may be exposed to the outside of the housing 211. According to an embodiment, at least a portion of the sensor module 300 may be exposed to the outside through a sensing opening 212 in the rear surface R of the housing 211.

The sensor module 300 may include a biometric sensor 320 on one surface of the circuit board 310. In the state in which most of the circuit board 310 is disposed inside the housing 211 to be hidden, at least a portion of the biometric sensor 320 may be disposed to be visible from the outside of the electronic device 200. According to an embodiment, the sensor module 300 may be disposed on the circuit board 310 to be oriented in the second (−Z) direction. When the electronic device 200 is worn on the corresponding body portion of the user, for example, the biometric sensor 320 may emit light toward the user's body portion and may receive light reflected by the user's body portion.

According to various embodiments, the biometric sensor 320 may include light emission unit (a light source or an emitter) 321 and at least one a light detector 322 or 323. Referring to FIG. 5, in the electronic device 200 according to an embodiment, the light emission unit 321 may be disposed in the center of the rear surface R of the housing 211, and at least one light reception member 322 or 323 may be disposed around the light emission unit 321. Of course, the various components constituting the biometric sensor 320 may have various other forms.

According to various embodiments, although not illustrated in the drawing, on the rear surface R of the housing 211, the biometric sensor 320 may further include at least one substantially transparent area (e.g., glass) such that light generated from the light emission unit 321 may be emitted to the outside.

Figure 6:
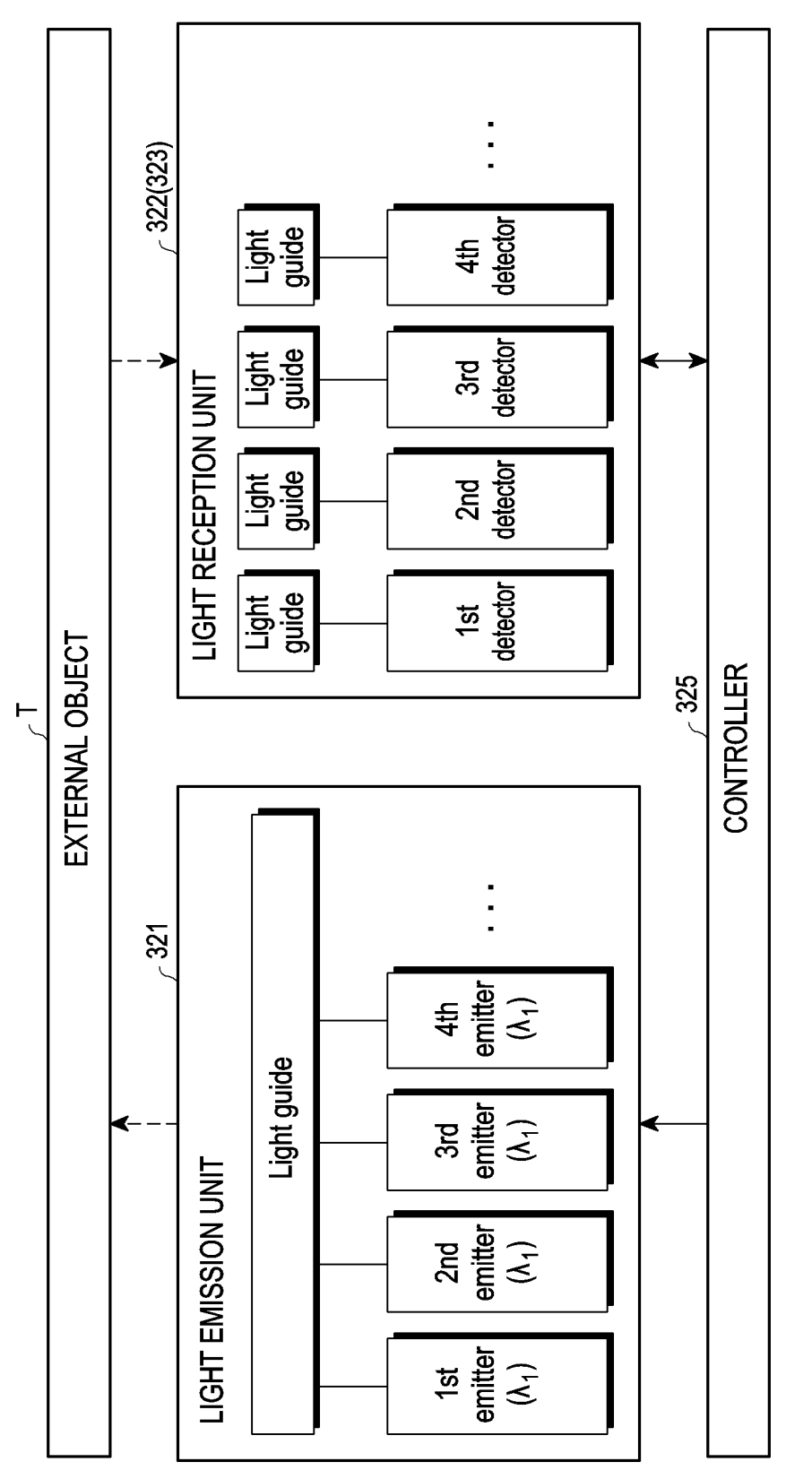
FIG. 6 is a block diagram illustrating an example relationship between a sensor module in an electronic device and an external object according to various embodiments.

FIG. 6 is a block diagram illustrating an example association relationship between a sensor module (e.g., the sensor module 300 in FIG. 5) in an electronic device (e.g., the electronic device 200 in FIG. 5) according to various embodiments and an external object T (e.g., the user's body portion (tissue)).

Referring to FIG. 6, the sensor module in the electronic device may include a light emission unit (e.g., a light source or an emitter including light emitting circuitry) 321, a light reception member (e.g., a detector or a sensor including light receiving circuitry) 323, and a controller (e.g., including processing circuitry) 325 for controlling the light emission unit and the light reception member.

According to various embodiments, the sensor module 300 of FIG. 5 may be configured in the form of a module connected to the controller 325 and/or a processor (e.g., the processor 120 in FIG. 1) or including at least some of the components thereof.

According to various embodiments, the controller 325 may include various processing circuitry and provide an electrical signal to control the operations of the light emission unit 321 and the light reception member 322 or 323, and may receive a signal received by the light reception member 322 or 323. The controller 325 may be connected to a processor (e.g., the processor 120 of FIG. 1) to control the intensity, driving channel, driving period, or the like of the light reception member 321.

According to various embodiments, each or one of the light emission unit 321 and the light reception member 322 or 323 may include a light guide (e.g., a compound parabolic concentrator (CPC) structure). The light guide may be disposed on the path of the light generated by the light emission unit 321 or the light incident on the light reception member 322 or 323 to deform each light (e.g., directional filtering) and to guide each light in the form of an optical signal (broken arrow) to interact with the skin (human tissue).

According to various embodiments, the light emission unit 321 may be configured to emit light having one wavelength or two or more wavelengths. The light emission unit 321 may include one or more light emitters including, for example, and without limitation, emitting diodes (LEDs), laser diodes (LDs), or the like, and respective LEDs and LDs may have different wavelengths. As another example, the light emission unit 321 may have a form in which several LEDs having the same wavelength are arrayed.

According to various embodiments, at least one light reception member 322 or 323 may be provided, and may receive light reflected by an object (e.g., the user's body portion) after being emitted from the light emission unit 322. For example, the light reception member may detect light reflected from or passing through a blood vessel in the skin. As another example, the light reception member 322 or 323 may determine the presence or absence of an object, or may image the shape of the object. The light reception member may include various detectors including, for example, and without limitation, a photodiode, an image sensor, or the like.

According to various embodiments, the processor (e.g., the processor 120 in FIG. 1) may control a biometric sensor (e.g., the biometric sensor 320 in FIG. 5) including the light-emission member 321 and the light reception member 322 or 323. For example, in the case of a sensor having a plurality of LEDs, it is possible to select an LED to be activated depending on the type or service of biometric measurement. As another example, a heart rate may be measured using a green LED and a red/IR LED may be activated in order to measure oxygen saturation (SpO$_2$). As another example, the intensity of the LED may be adjusted, or the gain of the light detector may be controlled depending on the color of the skin. As another example, a measurement cycle may be adjusted to, for example, once per 1 minute, once per 1 hour, or the like depending on a service, and detailed operations, such as whether to perform monitoring for 10 sec or to perform monitoring for 20 sec in one measurement session, may be controlled. Such operations may vary depending on the battery size, the power efficiency, the current consumption of a sensor, the use purpose, and the type of the electronic device.

Figure 7:
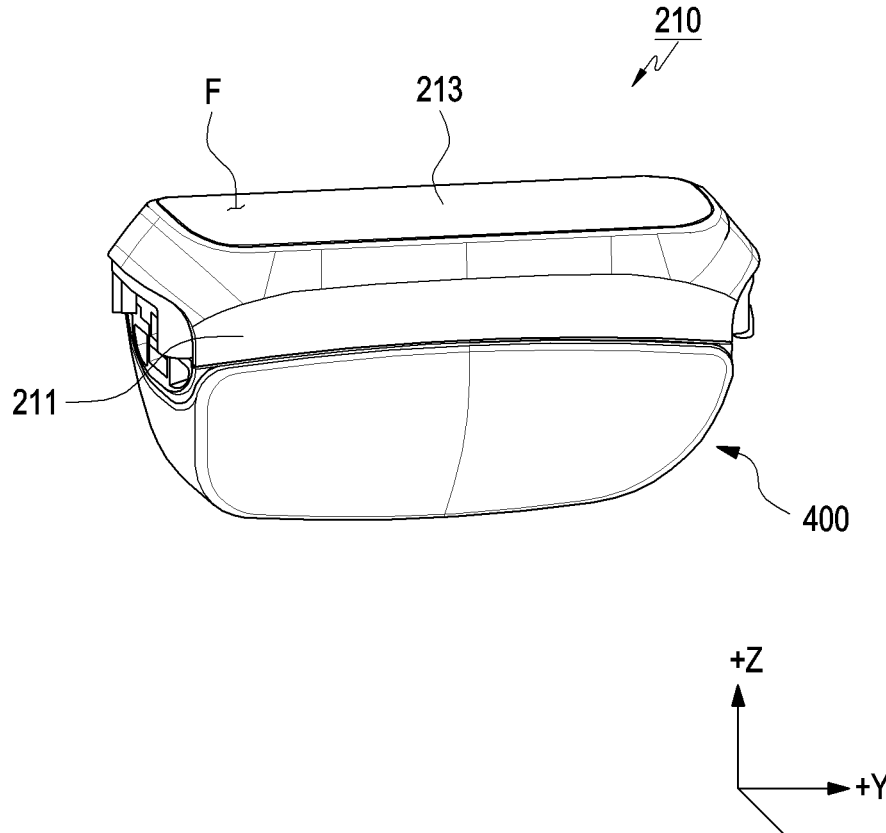
FIG. 7 is a perspective view illustrating an example electronic device and a charging device according to various embodiments.

FIG. 7 is a perspective view illustrating an example electronic device 200 and a charging device 400 according to various embodiments.

In FIG. 7, an electronic device 200 and a charging device 400 according to various embodiments are illustrated. The electronic device 200 and the charging device 400 may be partly or wholly the same in configuration as the electronic device 101 and the electronic device 102 of FIG. 1, respectively. The electronic device 200 and the charging device 400 may be coupled to configure a charging system for charging a battery (e.g., the battery 189 in FIG. 1) disposed in the electronic device 200.

The electronic device 200 and the charging device 400 may be provided as separate components, and may be configured to be coupled to each other as necessary. When the electronic device 200 and the charging device 400 are coupled to each other, it is possible to charge the battery (e.g., the battery 189 in FIG. 1) in the electronic device 200. According to various embodiments of the disclosure, although not separately illustrated in the drawing, in order to ensure that charging efficiency for the electronic device 200 is not lowered due to inter-device misalignment, the charging device 400 may have a shape corresponding to the appearance of the electronic device 200. Alternatively or additionally, the charging device 400 may be provided with means that is fixable when worn.

Referring to FIGS. 6 and 7, a charging terminal for electrical contact with the charging device 400 is not configured on the rear surface R of the electronic device 200 illustrated in FIG. 6. Therefore, the electronic device 200 and the charging device 400 according to various embodiments may basically configure a wireless charging system.

However, according to another embodiment, an electronic device (e.g., the electronic device 200 in FIG. 5) may be provided with a charging terminal for forming an electrical contact on the exterior of the housing 211, in which case, the charging device 400 may also be provided with a corresponding charging terminal and it is possible to perform not only wireless charging but also wired charging.

Figure 8:
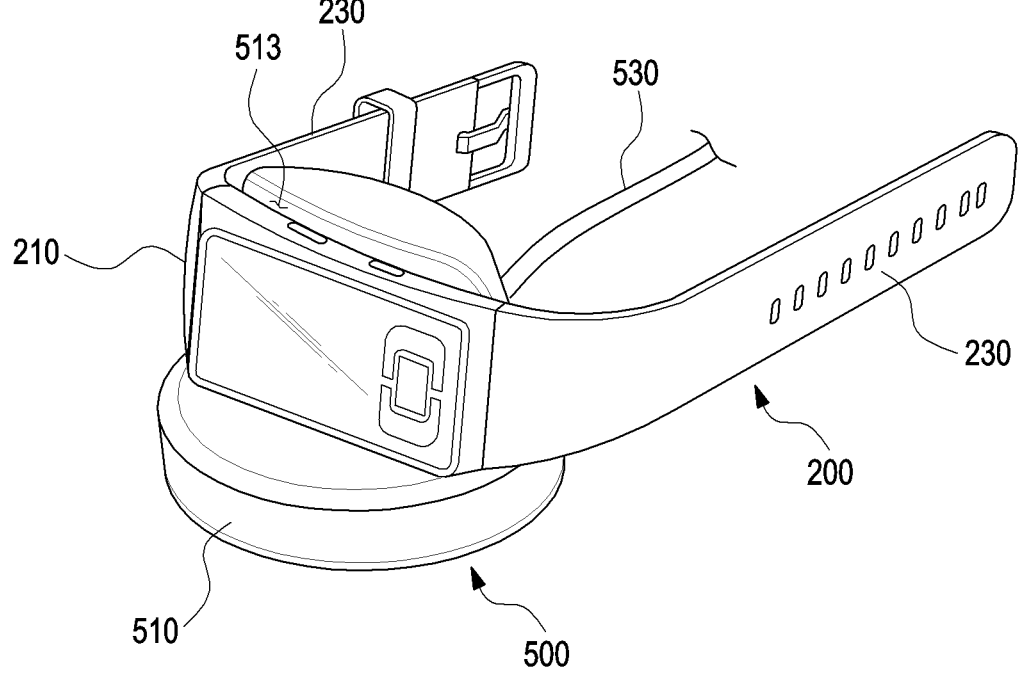
FIG. 8 is a perspective view illustrating an example electronic device and a charging device according to various embodiments.

FIG. 8 is a perspective view illustrating an example electronic device 200 and a charging device 500 according to various embodiments.

In FIG. 8, an electronic device 200 and a charging device 500 according to various embodiments are illustrated. The electronic device 200 and the charging device 500 may be partly or wholly the same in configuration as the electronic device 101 and the electronic device 102 of FIG. 1, respectively. The electronic device 200 and the charging device 500 may be coupled to configure a charging system for charging a battery (e.g., the battery 189 in FIG. 1) disposed in the electronic device 200.

According to various embodiments, the charging device 500 may include a main body 510 including a seating surface 513 on which at least part of the rear surface and/or the side surface of the electronic device 200 is seated, and a cable 530 connected to an external power source. According to various embodiments, the cable 530 may be configured to be attachable to/detachable from the charging device 500.

In this example embodiment, the electronic device 200 and the charging device 500 may be configured such that, when the electronic device 200 is placed on the seating surface 513 of the charging device 513, it is possible to charge the battery (e.g., the battery 189 in FIG. 1) in the electronic device 200. According to various embodiments of the disclosure, although not separately illustrated in the drawing, in order to ensure that charging efficiency for the electronic device 200 is not lowered due to inter-device misalignment, the charging device 500 may have a shape corresponding to the appearance of the electronic device 200. Alternatively or additionally, the charging device 500 may be provided with means that is fixable when worn.

As described above, a charging terminal for electrical contact with the charging device 400 is not configured on the rear surface R of the electronic device 200. Therefore, the electronic device 200 and the charging device 400 according to various embodiments may basically configure a wireless charging system.

However, even in the embodiment illustrated in FIG. 8, a wired charging method may be applied depending on the external configuration of the electronic device 200 (e.g., whether a charging terminal is provided on the exterior of the housing 211). For example, a charging terminal is exposed to the seating surface 513 of the charging device 500, and the charging terminal may be disposed to come into contact with at least one electrode exposed to the outside of the electronic device 200 to charge a battery (e.g., the battery 189 in FIG. 1) in the electronic device 200.

Figure 9:
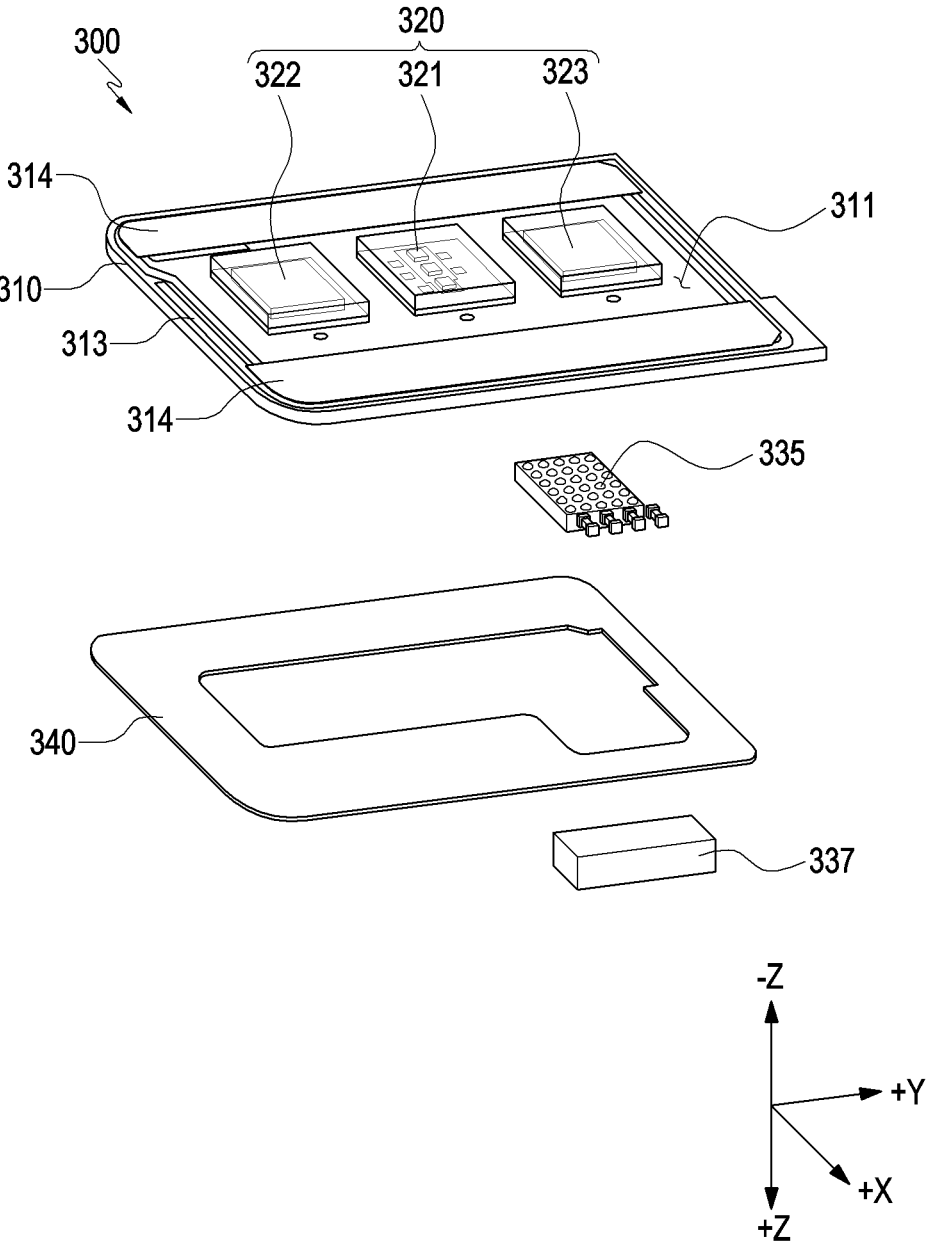
FIG. 9 is an exploded perspective view illustrating various elements of a sensor module according to various embodiments.

FIG. 9 is an exploded perspective view illustrating various elements of a sensor module 300 according to various embodiments.

According to various embodiments, the sensor module 300 may include a circuit board 310, a biometric sensor 320, a plurality of conductive lines and conductors 313 for wireless charging, and a shielding member 340.

The circuit board 310 may be disposed to face the rear surface of the housing 211. The circuit board 310 may include a first surface 311 oriented in a first (+Z) direction and a second surface 312 (e.g., the second surface 312 in FIG. to be described later) oriented in a second (−Z) direction that is opposite the first (+Z) direction. In addition, at least some components of the sensor module 300, for example, the biometric sensor 320, may be disposed on the first surface 311 of the circuit board 310.

According to various embodiments, FIG. 9 and the subsequent drawings illustrate the circuit board 310 as having a shape close to a rectangular shape when the circuit board 310 is viewed from above. However, it should be noted that this is merely an example and that the circuit board may have other various shapes. For example, the circuit board 310 may have a circular shape when viewed from above the circuit board 310.

The biometric sensor 320 may be, for example, a sensor that collects or measures one or more biometric signals from the user. It is possible to collect, using the biometric sensor 320, raw data for measuring, for example, and without limitation, one or more of the user's blood pressure, blood flow, heart rate (HRM, HRV), body temperature, respiration rate, oxygen saturation ($SpO_2$), cardiac tone, blood sugar, waist size, height, weight, body fat, calorie consumption, brainwaves, voice, skin resistance, electromyogram, electrocardiogram, gait, ultrasound image, sleep state, facial expression (face), pupil dilation, eye blinking, or the like.

According to an embodiment, the electronic device (e.g., the electronic device 200 in FIG. 5) may generate biometric information (or biometric characteristic information), and may analyze the biometric signals. For example, a pulse wave signal obtained through a heart rate variability (HRV) or heart rate monitor (HRM) sensor may be a biometric signal. The pulse wave signal may be a signal acquired through a photoplethysmography (PPG) sensor using an optical method or an electrocardiography (ECG) sensor using an electrode. According to an embodiment, since the biometric sensor 320 uses an optical method, the biometric sensor may correspond to the PPG sensor. When the biometric sensor 320 includes an electrode that is capable of applying an electrical stimulus for acquiring a biometric signal, the biometric sensor 320 may correspond to the ECG sensor. According to various embodiments, the electronic device 200 may obtain primary biometric information, such as an average heart rate or a heart rate distribution by analyzing the biometric signals, and may obtain secondary biometric information, such as a higher level of stress state or vascular aging degree, by processing the primary biometric information.

According to an embodiment, the electronic device 200 may merely output the user's biometric signals collected by the biometric sensor 320, and may output biometric information by analyzing the biometric signals through a processor built in the electronic device 200. According to various embodiments, the biometric signals may be transmitted to a processor within the biometric sensor 320, a processor (e.g., the processor 120 in FIG. 1) of the electronic device 200 having an biometric sensor module embedded therein, or a processor of an external device (e.g., the server 108 or the electronic device 104 in FIG. 1), and may be used for generating biometric information.

According to various embodiments, when the user wears the electronic device 200, the biometric sensor 320 needs to be close to the corresponding body portion (e.g., a wrist) to increase sensing accuracy. Thus, the light emission unit 321 and the light reception members 322 and 323 of the biometric sensor 320 may be disposed to be adjacent to the rear surface R of the housing 211.

As some components of the biometric sensor 320, at least one light emission unit 321 may be disposed on the circuit board 310. The light emission unit 321 may emit light toward the rear surface R of the housing 211. For example, the light emission unit 321 may include an LED module, and the light emission unit 321 may emit light having various colors. The emitted light may have a wavelength in the range of, for example, about 380 nm to 800 nm. As another example, the light emitted from the light emission unit 321 may be green light, and may have a wavelength in the range of about 492 nm to 575 nm. According to various embodiments, as illustrated in FIG. 9, in order to protect an internal circuit board that emits light, the light emission unit 321 may be capped in the peripheral portion of the circuit board. The capping material may be, for example, epoxy.

According to various embodiments, when the light emitted from the light emission unit 321 is reflected by the user's body, the light reception members 322 and 323 may receive the reflected light and may convert the light into current. For example, in order to measure the user's heartbeat, when a part of the light emitted from the light emission unit 321 is reflected by the user's intravascular blood flow and is returned to the light reception members 322 and 323, the light reception members 322 and 323 may convert the returned light into a current signal. As another example, since it is efficient to form a light reception member to have a large area in order to sufficiently receive the reflected light, a plurality of light reception members 323 and 333 may be around the light emission unit 321. For example, as illustrated in FIG. 9, two light reception members 322 and 323 may be disposed at the opposite lateral sides of the light emission unit 321. However, the arrangement of the light reception members 322 and 323 is not limited thereto, and the arrangement and number of the right reception units may be variously changed to efficiently receive light reflected from the corresponding body portion of the user and to efficiently receive the user's biometric information. As another example, three or more light reception members may be disposed along the periphery of the light emission unit 321.

According to various embodiments, the light emission unit 321 and the light reception members 323 may be disposed on the same plane. For example, the light emission unit 321 electrically connected to the circuit board 310 may be disposed on the first surface 311 oriented in the second (−Z) direction in the circuit board 310, and the light reception members 322 and 323 may be disposed to be spaced apart from each other by a predetermined distance with the light emission unit 321 interposed therebetween. As described above, a plurality of light reception members 322 and 323 may be provided, and the plurality of light reception members 322 and 323 may be disposed on the first surface 311 of the circuit board 310 and may be electrically connected to a first circuit board. According to various embodiments, the plurality of light reception members 322 and 323 may be disposed to surround the light emission unit 321 on the same plane as the light emission unit 321. For example, as illustrated in FIG. 9, the light emission unit 321 may be disposed in the central portion of the first surface 311 of the circuit board 310, and the plurality of light reception members 322 and 323 may be disposed to be spaced apart from the light emission unit 321 by substantially the same distance with the light emitting part 321 interposed therebetween. The arrangement of the light emission unit 321 and the light reception members 322 and 323 may be variously specified according to an embodiment.

The circuit board 310 may include a conductive line 313 and a plurality of conductors for wireless charging. The conductive line 313 may serve as a wireless charging antenna radiator. According to an embodiment, the conductive line 313 may receive a wireless charging signal using NFC. For example, a near-field communication (NFC) antenna, which transmits/receives a wireless signal in an NFC manner, may be configured using the conductive line 313. As another example, a magnetic secure transmission (MST) antenna, which transmits/receives a wireless signal in an MST manner, may be configured using the conductive line 313. In addition to the above-described embodiments, the conductive line 313 may be applied to various other wireless signal methods using induction or resonance.

The conductive line 313 may be disposed on one surface (e.g., the first surface 311) of the circuit board 310. The conductive line 313 may be electrically connected to other conductors and/or electronic components (e.g., the processor 335) on the circuit board 310. According to various embodiments, the conductive line 313 may generate current by electromagnetic induction occurring from an external electronic device (e.g., the charging device 400 in FIG. 7 or the charging device 500 in FIG. 8). The current generated in the conductive line 313 may charge a battery (e.g., the battery 189 in FIG. 1) through the circuit board 310.

According to various embodiments, the circuit board 310 may be a multilayer circuit board formed by stacking a plurality of sub circuit boards. There may also be provided a plurality of conductive lines 313, and the conductive lines 313 may be disposed on at least two circuit boards among the plurality of sub circuit boards. According to an embodiment, the conductive line 313 may be disposed on each of the sub circuit boards. Each of the plurality of sub circuit boards may be electrically connected to another one of the sub circuit boards stacked on each other via at least one conductive via. Similarly, each of the conductive lines may be connected to another conductive line disposed on another layer. This will be described in greater detail below with reference to FIG. 13.

The second surface (e.g., the second surface 312 of FIG. 10B to be described in greater detail below) of the circuit board 310 may further include at least one electronic component (e.g., the processor 335). In the electronic device 200 according to various embodiments, components for performing the wireless charging function and electronic components electrically connected to the biometric sensor may be integrated into the single circuit board 310. By integrating the wireless charging function and the biometric information sensing function into the single circuit board 310, it is possible to simplify the structure and to miniaturize the module, and with the size reduction of the main components and related components, it is possible to reduce the size of the electronic device 200.

According to an embodiment, the sensor module 300 may include a first protection member 314 on one surface side of the circuit board 310, and, according to another embodiment, the sensor module 300 may further include a second protection member 337 on the other surface side of the circuit board 310.

According to an embodiment, the first protection member 314 may be a component located on at least a portion on the first surface 311 of the circuit board 310. Alternatively, although not illustrated in the drawing, the first protection member 314 may be a portion to be attached (or seated) to the inner surface of the housing 210.

According to various embodiments, the first protection member 314 may include a bonding material and/or a shock absorption material. The first protection member 314 may include, for example, an attachable material, such as, bond, tape, double-sided tape, sheet, or release paper, and may include a shock absorption or elastic material, such as Poron, sponge, or rubber. According to an embodiment, as illustrated in FIG. 9, a plurality of first protection members 314 may be provided on the first surface 311 of the circuit board 310 at different positions. According to another embodiment, the first protection member 314 may include a plurality of first protection members 314 at one position, and may overlap each other. According to various embodiments, the first protection member 314 may include a light blocking material to prevent and/or reduce light leakage of the light emission unit 321.

According to various embodiments, the second protection member 337 is disposed on the second surface 312 of the circuit board 310, and may be a component for protecting electronic components (e.g., a processor or a sensor IC 335) disposed inside of the sensor module from other electronic components disposed outside the biometric sensor or a counterpart The second protection member 337 may include a shock absorption or elastic material such as Poron, sponge, or rubber.

The shielding member 340 may be disposed on the second surface (e.g., the second surface 312 in FIGS. 10A and 10B to be described later) of the circuit board 10. The shielding member 340 may be configured to block noise that interferes with a wireless communication signal received through the conductive line 313 from other electronic components disposed outside the sensor module 300.

Figures 10A, 10B:
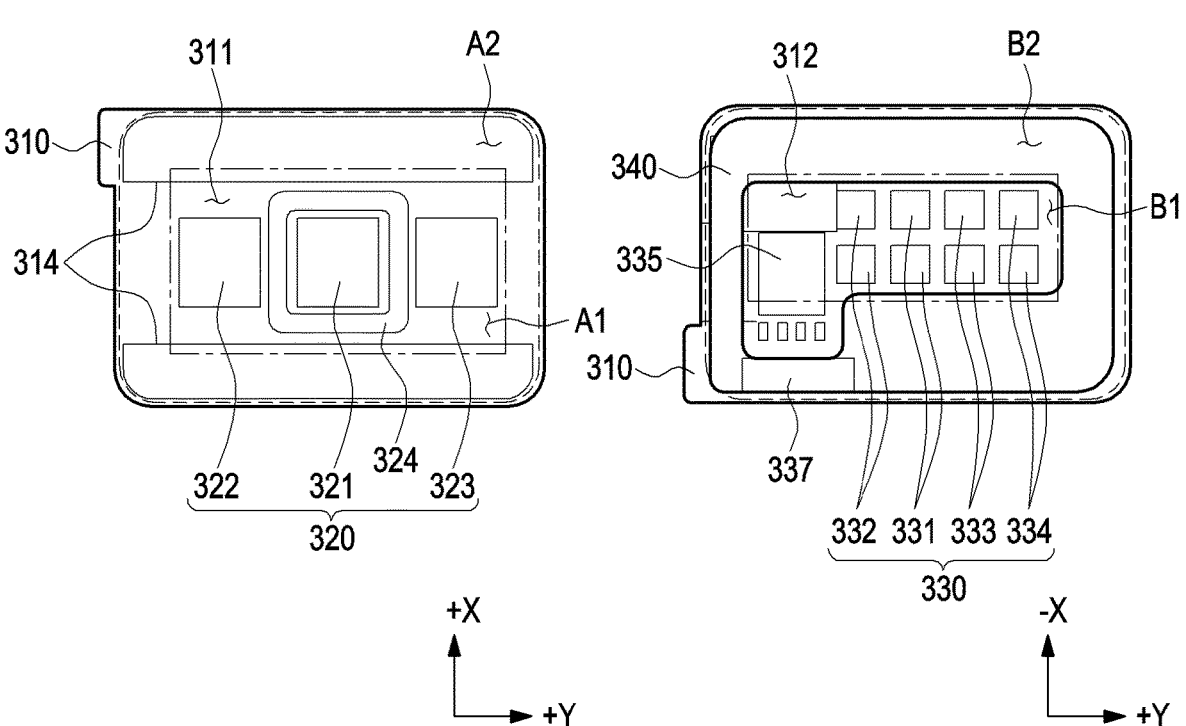
FIG. 10A is a diagram illustrating an example circuit board viewed from above a first surface according to various embodiments.
FIG. 10B is a diagram illustrating the example circuit board viewed from above a second surface according to various embodiments.

FIG. 10A is a diagram illustrating an example circuit board 310 according to various embodiments when the circuit board 310 is viewed above a first surface 311 of the circuit board 310, and FIG. 10B is a diagram illustrating the circuit board 310 according to various embodiments when the circuit board 310 is viewed above a second surface 312.

Referring to FIG. 10A, the circuit board 310 is illustrated in which the circuit board 310 is viewed from above the first surface 311. In FIG. 10A, some components (e.g., the conductive line 313 in FIG. 9) may be omitted for convenience.

On the first surface 311 of the circuit board 310, a biometric sensor 320 including a light emission unit 321 and light reception members 322 and 323 may be disposed. According to various embodiments, a wall 324 may be disposed between the light emission unit 321 and the light reception member 322. The wall 324 may be configured to prevent and/or reduce light other than the light, which is reflected from the light emitted from the light emission unit 321, from being received by the light reception members 322 and 323. A recess may be formed inside the wall 324. According to an embodiment, the sensor module 300 may acquire biometric information using a principle in which, in the state in which the light emission unit 321 is disposed in the recess, light emitted from the light emission unit 321 reaches an external object through a substantially transparent portion (e.g., glass) in the rear surface R of the electronic device (e.g., the electronic device 200 in FIG. 5) and then a part of the light is reflected from the external object to be incident on the light reception members 322 and 323 again. To this end, the height of the partition structure 324 may be higher than the height of the light emission unit 321 and the light reception members 322 and 323.

When the sensor module 300 is viewed from above the first surface 311, an antenna area (ANT area) is formed by a second area A2 in the edge portion of the sensor module 300, and a sensor area is formed by a first area A1 in the central portion of the first surface 311. In the first area A1, the light emission unit 321, the light reception members 322 and 323, and/or the wall 324, which have been described above with reference to FIG. 10A, may be disposed. In the second area A2, the conductive line 313 (e.g., a loop antenna), which has been described above with reference to FIG. 9, may be disposed.

Referring to FIG. 10A, the circuit board 310 is illustrated in which the circuit board 310 is viewed from above the second surface 311. In FIG. 10B, some components (e.g., the conductive line 313 in FIG. 9) may be omitted for convenience.

When the sensor module 300 is viewed from above the second surface 312, a plurality of conductors 331, 332, 333, and 334 and electronic components (e.g., a processor or a sensor IC 335) may be disposed on the second surface 312.

When the sensor module 300 is viewed from above the first surface 312, a blocking area is formed by a fourth area B2 in the edge portion of the sensor module 300, and an energy and data transmission area may be formed by a third area B1 in the central portion of the second surface 312. In the third area B1, a plurality of conductors 331, 332, 333, and 334 and electronic components (e.g., a processor or a sensor IC 335) may be disposed. According to an embodiment, a part of the conductive line 313 (e.g., a loop antenna) may be formed in the fourth area B2. A shielding member 340 may be disposed in the fourth area B2. The shielding member 340 may be formed of a ferrite sheet to prevent and/or reduce a charging signal received by the sensor module 300 from interfering with noise generated from electronic components located outside the sensor module 300.

Figure 11:
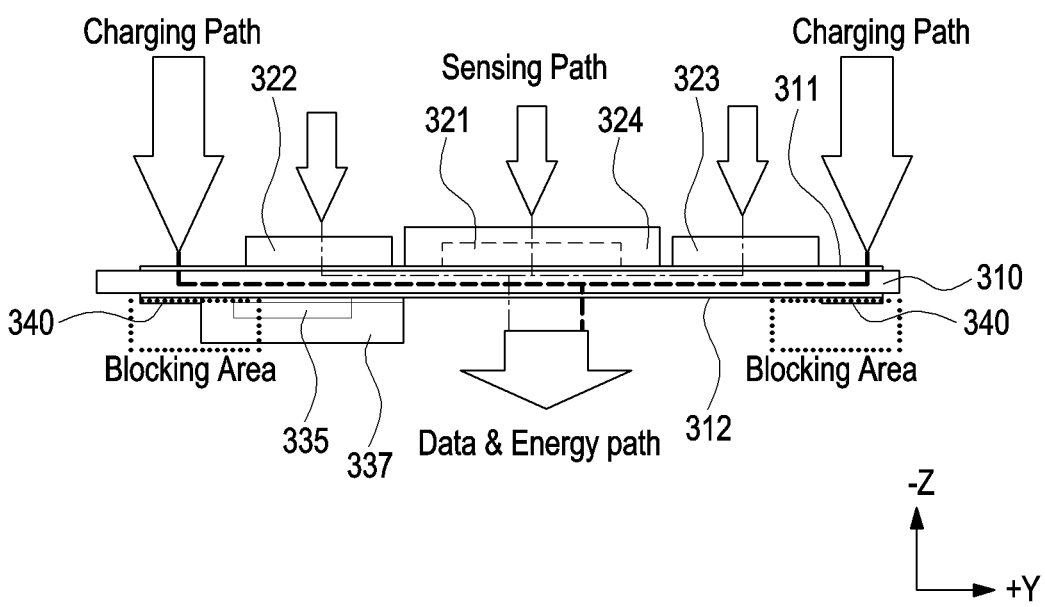
FIG. 11 is a diagram illustrating example paths through which a biometric information signal and a charging signal are transmitted in a sensor module according to various embodiments.

FIG. 11 is a cross-sectional diagram illustrating example paths through which a biometric information signal and a charging signal are transmitted in the sensor module 300 according to various embodiments.

Referring to FIGS. 10A and 10B and FIG. 11, in the sensor module 300, the light emission unit 321, the light reception members 322 and 323, and/or the wall 324 may be disposed in the central area (e.g., the first area A1 illustrated in FIG. 10A) of the first surface 311 of the circuit board 310. The biometric information signal may pass through the inside of the circuit board 310 along the conductive paths of the light reception members 322 and 323 located in the central area (e.g., the first area A1 illustrated in FIG. 10A) of the first surface 311. The biometric information signal may be transmitted to the outside (e.g., the first processor 120 in FIG. 1) of the sensor module 300 through the transmission area (e.g., the third area B1 illustrated in FIG. 10B) located in the central area of the second surface 312 of the circuit board 310.

In the sensor module 300, the shielding member 340 may be disposed in the edge area (e.g., the fourth area B2 illustrated in FIG. 10B) of the second surface 312 of the circuit board 310. The charging signal may receive energy (e.g., energy generated by electromagnetic induction or resonance) through a conductive line (e.g., the conductive line 313 in FIG. 9) disposed in the edge area of the circuit board 310, and may pass through the inside of the circuit board 310 along the conductive path of the conductive path of the conductive line (the conductive line 313 of FIG. 9). The charging signal may be transmitted to the outside (e.g., the battery 189 in FIG. 1) of the sensor module 300 through the transmission area (e.g., the third area B1 illustrated in FIG. 10B) located in the central area of the second surface 312 of the circuit board 310.

Figures 12A, 12B, 12C, 12D:
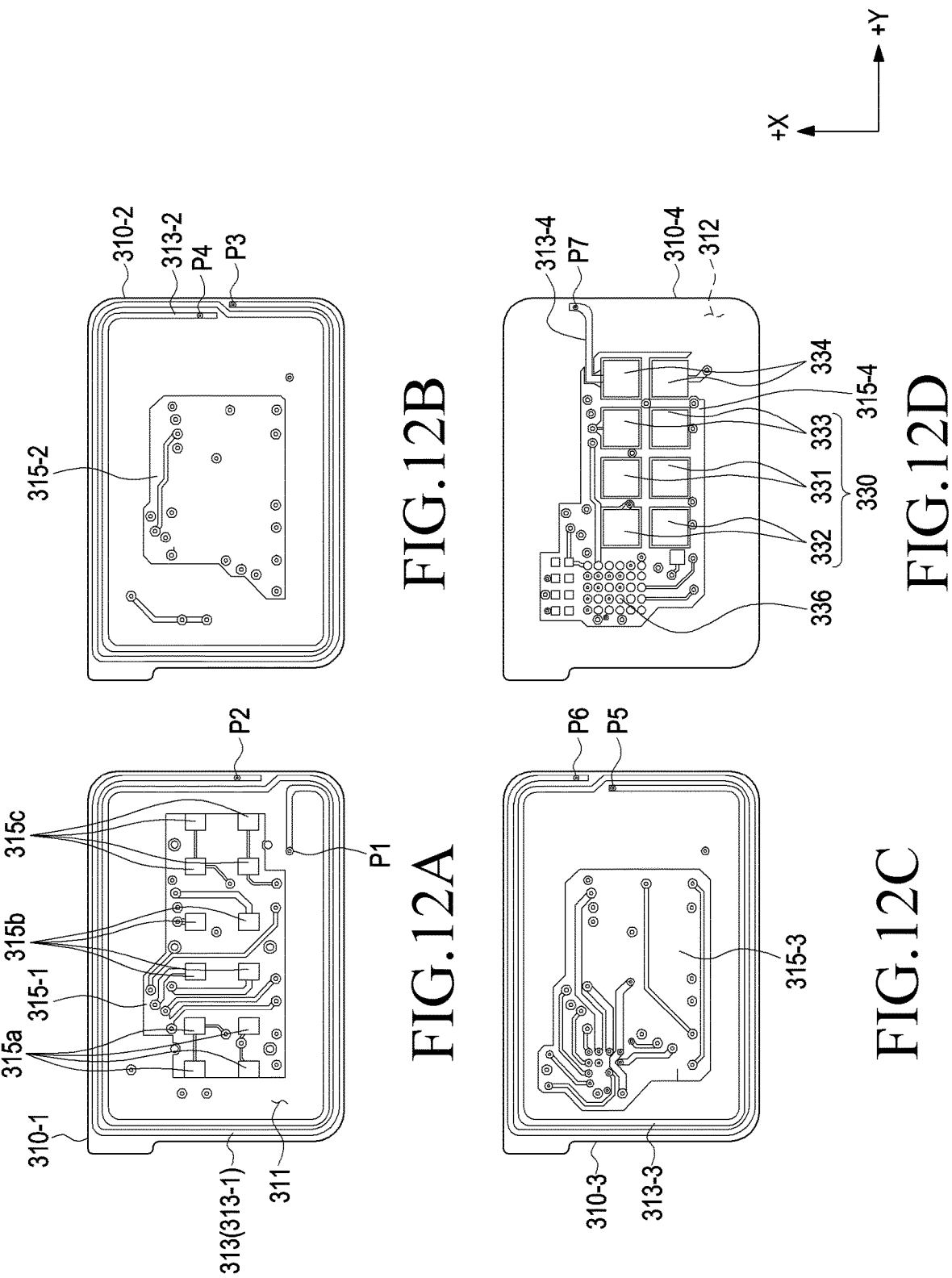
FIG. 12A is a diagram illustrating an example sub circuit board included in a circuit board included in an electronic device according to various embodiments.
FIG. 12B is a diagram illustrating an example sub circuit board included in a circuit board included in an electronic device according to various embodiments.
FIG. 12C is a diagram illustrating an example sub circuit board included in a circuit board included in an electronic device according to various embodiments.
FIG. 12D is a diagram illustrating an example sub circuit board included in a circuit board included in an electronic device according to various embodiments.

FIGS. 12A, 12B, 12C and 12D are diagrams illustrating a plurality of example sub circuit boards 310-1, 310-2, 310-3, and 310-4 of a circuit board 310 included in an electronic device (e.g., the electronic device 200 in FIG. 5) according to various embodiments. FIG. 12A illustrates a first example sub circuit board 310-1, FIG. 12B illustrates a second example sub circuit board 310-2, FIG. 12C illustrates a third example sub circuit board 310-3, and FIG. 12D illustrates a fourth example sub circuit board 310-4.

The plurality of sub circuit boards 310-1, 310-2, 310-3, and 310-4 may be stacked in the same direction (e.g., in the second (−Z) direction in FIG. 9). Each sub circuit board may be directly stacked on another adjacent sub circuit board, or may be stacked in the state in which an insulator surrounding at least a portion of each sub-substrate is interposed between adjacent sub circuit boards.

According to various embodiments, one surface of the first sub circuit board 310-1 may be a surface that forms the first surface 311 of the circuit board 310. According to an embodiment, a first conductive plate 315-1 may be disposed on the first sub circuit board 310-1, and a plurality of conductors 315a, 315b, and 315c, a plurality of conductive vias, and conductive lines connecting at least some of the plurality of conductive vias may be formed on the first conductive plate 315-1. According to an embodiment, each of the plurality of conductors 315a, 315b, and 315c formed on the first sub circuit boards 315-1 may be configured to electrically connect the light emission unit 321 and the light reception members 322 and 323 illustrated in FIG. 9 to the circuit board 310. In addition to the conductive lines connecting at least some of the plurality of conductive vias, the first sub circuit board 310-1 may include a first conductive line 313-1 for wireless charging, in which the first conductive line 313-1 is wound by at least one turn around the edges of the first sub-substrate 310-1.

According to various embodiments, the circuit board 310 may include a second sub circuit board 310-2 disposed below the first sub circuit board 310-1 (e.g., in the first direction (Z-axis direction) in FIG. 9). A second conductive plate 315-2 may be disposed on the second sub circuit board 310-2. On the second conductive plate 315-2, a plurality of conductive vias and conductive lines connecting at least some of the plurality of conductive vias may be formed. In addition to the conductive lines connecting at least some of the plurality of conductive vias, the second sub circuit board 310-2 may include a second conductive line 313-2 for wireless charging, in which the second conductive line 313-2 is wound by at least one turn around the edges of the second sub-substrate 310-2.

According to various embodiments, the circuit board 310 may include a third sub circuit board 310-3 disposed below the second sub circuit board 310-2 (e.g., in the first direction (Z-axis direction) in FIG. 9). A third conductive plate 315-3 may be disposed on the third sub circuit board 310-3. On the third conductive plate 315-3, a plurality of conductive vias and conductive lines connecting at least some of the plurality of conductive vias may be formed. In addition to the conductive lines connecting at least some of the plurality of conductive vias, the third sub circuit board 310-3 may include a third conductive line 313-3 for wireless charging, in which the third conductive line 313-3 is wound by at least one turn around the edges of the third sub-substrate 310-3.

According to various embodiments, the circuit board 310 may include a fourth sub circuit board 310-4 disposed below the third sub circuit board 310-3 (e.g., in the first direction (Z-axis direction) in FIG. 9). One surface of the fourth sub circuit board 310-4 may be a surface that forms the second surface 312 of the circuit board 310. According to an embodiment, a fourth conductive plate 315-4 may be disposed on the fourth sub circuit board 310-4, and a plurality of conductors 330 and 334, a plurality of conductive vias, and conductive lines connecting at least some of the plurality of conductive vias may be formed on the fourth conductive plate 315-4. According to an embodiment, some of the plurality of conductors 334 formed on the fourth conductive plate 315-4 may be configured to be electrically connected to the conductive line 313-4 for wireless charging. Other components 330 except for some components 334 among the plurality of conductors may be components for electrically connecting the light emission unit 321 and the light reception members 322 and 323 illustrated in FIG. 9 to the electronic components (e.g., the processor or the sensor IC 335) included in the sensor module 300. According to an embodiment, the plurality of conductors 330 and 334 disposed on the fourth conductive plate 315-4 may be electrode pads.

According to an embodiment, FIGS. 12A, 12B, 12C and 12D illustrate that the conductive line 313-4 for wireless charging is only linearly connected to the inner conductors 334 in the edge area of the circuit board 310, but the embodiment is not limited thereto. According to another embodiment, as illustrated in FIGS. 12A, 12B, and 12C, the conductive line 313-4 for wireless charging may have a shape that at least partially extends along the edge area of the circuit substrate 310 and is then lead into the central area of the circuit board 310.

According to various embodiments, the circuit board 310 includes a plurality of sub circuit boards 310-1, 310-2, 310-3, and 310-4, and a conductive plate 315-1, 315-2, 315-3, or 315-4, and a conductive line 313-1, 313-2, 313-3, or 313-4 for wireless charging may be disposed on at least one of the plurality of sub circuit boards 310-1, 310-2, 310-3, and 310-4. The conductive lines 313-1, 313-2, 313-3, and 313-4 for the wireless charging are respectively spaced apart from the conductive plates 315-1, 315-2, 315-3, and 315-4 by a predetermined distance. According to an embodiment, the conductive lines 313-1, 313-2, 313-3, and 313-4 may be disposed in an area corresponding to the blocking area mentioned in FIG. 10, thereby preventing and/or reducing a charging signal received by a sensor module (e.g., the sensor module 300 in FIG. 11) from interfering with noise generated from electronic components located outside the sensor module (e.g., the sensor module 300 in FIG. 11).

Referring to FIGS. 12A, 12B, 12C and 12D, some of the plurality of conductive lines 313-1, 313-2, 313-3, and 313-4 disposed on the circuit board 310 may be wound by a predetermined number of turns in order to secure antenna performance. Accordingly, the conductive lines disposed on one of the plurality of sub circuit boards 310-1, 310-2, 310-3, and 310-4 may be electrically connected to the conductive lines disposed on another sub circuit board stacked adjacent thereto. For example, the conductive line 313-1 disposed on the first sub circuit board 310-1 may be electrically connected to the conductive line 313-2 disposed on the second sub circuit board 310-2.

According to various embodiments, high charging efficiency may be obtained only when current flowing in a predetermined direction is generated when a conductive line 313-1, 313-2, 313-3, or 313 disposed on at least one of the plurality of sub circuit boards 310-1, 310-2, 310-3, and 310-4 generates a wireless charging signal due to electromagnetic induction by an external electronic device (e.g., the charging device 400 in FIG. 7 or the charging device 500 in FIG. 8). For high charging efficiency, the conductive lines 313-1, 313-2, 313-3, and 313-4 according to various embodiments may be designed to be wound in a predetermined direction (e.g., clockwise) on the sub circuit boards, respectively. Conductive lines formed on a sub circuit board may be electrically connected to conductive lines disposed on another adjacent sub circuit board through conductive vias. According to some embodiments, when the conductive line is wound in a predetermined direction, an antenna area in which the conductive line is disposed may gradually expand in an adjacent sub circuit board. For example, when the conductive line is set to be wound around a sub circuit board in a direction from the inside of the sub circuit board to the edge of the sub circuit board substrate in each of the sub circuit boards, the size of the sub circuit board may be increased or the first area (e.g., the antenna area A1) described above with reference to FIG. 10A may be increased.

According to various embodiments, it is possible to ensure the antenna performance without increasing the size of the circuit board 310. For example, an input terminal (e.g., P1) and an output terminal (e.g., P2) of a conductive line (e.g., the first conductive line 313-1) disposed on one of the plurality of sub circuit boards 310-1, 310-2, 310-3, and 310-4 may be disposed at an inner side and an outer side of the one sub circuit board, respectively. An input terminal (e.g., P3) and an output terminal (e.g., P4) of a conductive line (e.g., the second conductive line 313-2) disposed on another sub circuit board (e.g., the second sub circuit board 310-2) stacked adjacent to the one sub circuit board may be disposed at an outer side and an inner side of the another sub circuit board, respectively. For example, assuming that the winding direction of the first conductive line 313-1 disposed on the first sub circuit board 310-1 is directed from the inner side of the first sub circuit board 310 toward the edge of the first sub circuit board 310-1 (in→out), the winding direction of the second conductive line 313-2 disposed on the second sub circuit board 310-2 may be designed to be directed from the outer side of the second sub circuit board 310-2 toward the inner side of the second sub circuit board 310-2 (out→in).

In the above-described embodiment, two sub circuit boards (e.g., the first sub circuit board 310-1 and the second sub circuit board 310-2) have been described as an example, but the above-described embodiments are applicable to three or more sub circuit boards. For example, the first conductive line 313-1 disposed on the first sub circuit board 310-1 may be designed to extend while surrounding the circumference of the first conductive plate 315-1 and to be wound from the inner side of the first sub circuit board 310-1 toward the edge of the first sub circuit board 310-1 (in→out). In this case, the input terminal P1 of the first conductive line 313-1 may be disposed at the inner side of the first sub circuit board 310-1 compared to the output terminal P2. In addition, the second conductive line 313-2 disposed on the second sub circuit board 310-2 may be designed to extend while surrounding the circumference of the second conductive plate 315-2 and to be wound from the outer side of the second sub circuit board 310-2 toward the inner side of the second sub circuit board 310-2 (out→in). In this case, the input terminal P3 of the second conductive line 313-2 may be disposed at the inner side of the second sub conductive line 310-2 compared to the output terminal P4. The third conductive line 313-3 disposed on the third sub circuit board 310-3 may be designed to extend while surrounding the circumference of the third conductive plate 315-3 and to be wound from the inner side of the third sub circuit board 310-3 toward the outer side of the third sub circuit board 310-3 (out→in). In this case, the input terminal P5 of the third conductive line 313-3 may be disposed at the inner side of the third sub circuit board 310-3 compared to the output terminal P6. In this way, the first conductive line 313-1 may be configured to be wound from the inner side toward the outer side (in→out), the second conductive line 313-2 may be configured to be wound from the outer side toward the inner side (out→in), and the third conductive line 313-3 may be configured to be wound from the inner side toward the outer side again (in→out). the output terminal P6 of the third conductive line 313-3 may be electrically connected with the terminal P7 of the fourth sub circuit board 310-4. According to various embodiments, the sizes of the plurality of sub circuit boards 310-1, 310-2, 310-3, and 310-4 may be set to be substantially the same. For example, the sizes of the first sub circuit board 310-1 and the second sub circuit board 310-2 may be substantially the same. According to various embodiments, the conductive lines may be designed to be wound by a predetermined number of turns on sub circuit boards, respectively. For example, the number of turns (e.g., twice) of the first conductive line 313-1 may be the same as the number of turns (e.g., twice) of the second conductive line 313-2.

In the disclosure, since the winding directions of adjacent conductive lines are changed on adjacent layers, it is possible to configure the censor module to be compact by limiting the increase in the size of the sub circuit board or the size of the antenna area according to the design of the conductive lines included in respective sub circuit boards.

Figure 13:
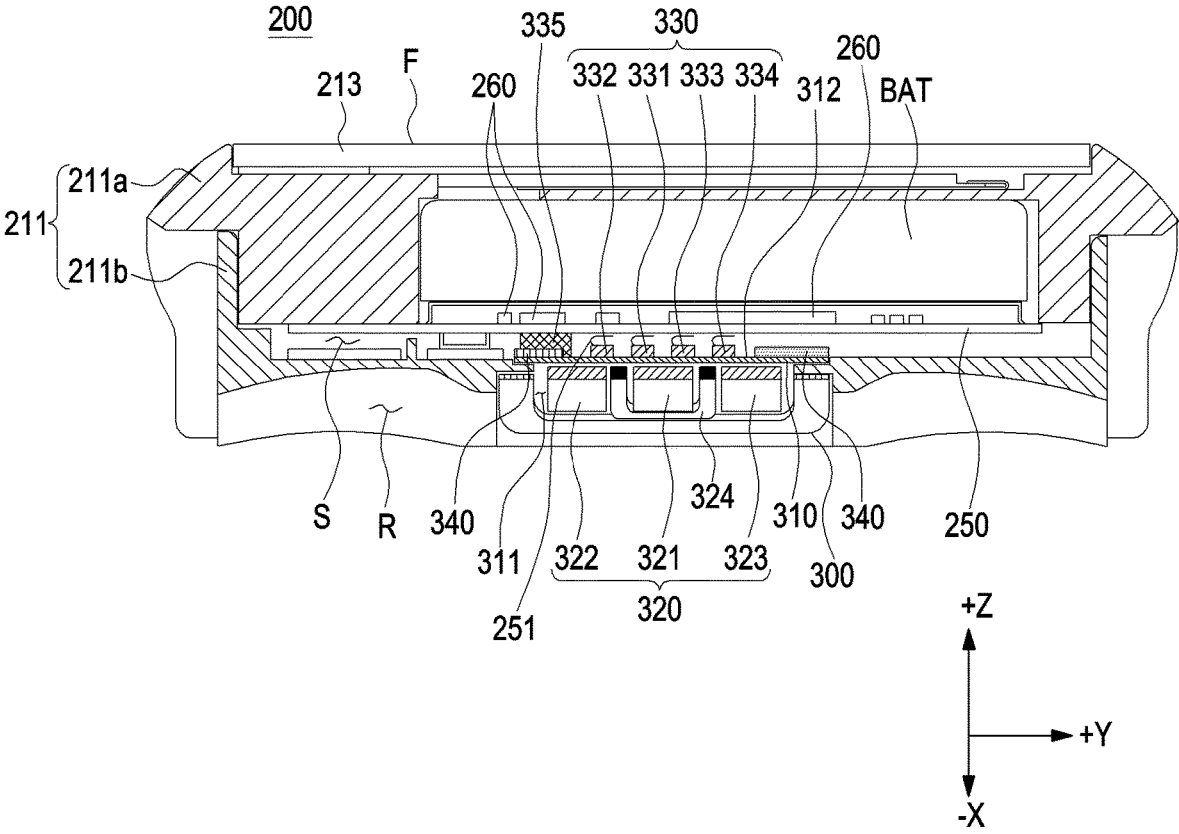
FIG. 13 is a cross-sectional view illustrating an example electronic device according to various embodiments.

FIG. 13 is a cross-sectional view illustrating an example electronic device 200 according to various embodiments.

According to various embodiments, the electronic device 200 may include a housing 211, and a main circuit board 250 and a battery BAT within the housing 211, and may include a sensor module 300.

According to various embodiments, the second housing 210 may be configured at least partially or wholly the same as the first housing 211 described above with reference to FIG. 2. According to an embodiment, the housing 211 may include an upper housing 211a and a lower housing 211b. According to an embodiment, in the housing 211, the upper housing 211a and the lower housing 211b may be firmly coupled to each other since at least a part of the upper housing 211a and at least a part of the lower housing 211b are engaged with each other. The electronic device 200, in which the upper housing 211a and the lower housing 211b are coupled to each other, may have a space S therein. Various components including the main circuit board 250, the battery BAT, and the sensor module 300 may be disposed in the space S.

According to various embodiments, a circuit board may be disposed in the inner space S of the housing 211. Referring to FIG. 13, the electronic device 200 may further include a main circuit board 250 (hereinafter, referred to as a "second circuit board 250") in addition to a circuit board 310 (hereinafter, referred to as a "first circuit board 310") of the sensor module 300.

On the second circuit board 250, a processor (e.g., the processor 120 in FIG. 1), a communication module (e.g., the communication module 190 in FIG. 1), and the like may be in the form of integrated circuit chips. The second circuit board 250 may be electrically connected to a battery (e.g., the battery 189 in FIG. 1) disposed in the housing 211. According to various embodiments, the second circuit board 250 may be electrically connected to various electronic components 260 through a connector (not illustrated).

According to various embodiments, a heat dissipation structure and/or a blocking structure may be provided between the second circuit board 250 and the battery BAT. For example, the heat dissipation structure may receive heat generated from the main circuit board 250, thereby preventing and/or avoiding the battery BAT from being overheated. For example, the blocking structure (e.g., a shield can) may prevent and/or reduce noise of components around the second circuit board 250 from being received by the various electronic components 260 on the second circuit board 250.

According to various embodiments, various electronic components included in the electronic device 200 may be separately disposed on the first circuit board 310 and the second circuit board 250. Through this, it is possible to improve the mounting efficiency of electronic components. For example, a component for acquiring a biometric information signal and a component for acquiring a wireless charging signal may be disposed on the first circuit board 310, and various components for performing other functions of the electronic device 200 may be disposed on the second circuit board 250. As another example, components vulnerable to noise (e.g., conductive lines 313 included in the sensor module 300) and noise generating components (e.g., the electronic components 260) may be separately disposed on different circuit boards, respectively. As another example, components sensitive to impact and shock induction components may be separately disposed on different circuit boards, respectively. The above-described internal arrangement of the electronic components may naturally separate a noise generation section and a noise-sensitive section, and, for example, vibration shocks transmitted through one substrate may be blocked in another substrate section, thereby optimizing the electrical performance and durability of the electronic device.

According to various embodiments, the second circuit board 250 may be disposed in the space S between a first surface F (e.g., the front surface F in FIG. 2) and a second surface R (e.g., the rear surface in FIG. 4) of the electronic device 200. According to an embodiment, one surface of the second circuit board 250 may be disposed to face the second surface R of the electronic device 200.

According to various embodiments, by disposing one surface of the first circuit board 310 to face the second surface R of the electronic device 200, the one surface of the first circuit board 310 may be disposed parallel to the second circuit board 250.

According to various embodiments, the electronic device 200 may further include connection members 251 for electrically connecting the first circuit board 310 and the second circuit board 200 to each other. The connection members 251 may include, for example, a C-clip, a pogo pin, a connector, or the like. In addition, the connection members 251 may include various components as long as the components are configured to connect a circuit board and a circuit board, to connect a board and a component, or to connect a component and a component. As illustrated in FIG. 13, in the electronic device 200 according to an embodiment, electrode pads are disposed on the second surface 312 of the first circuit board 310, and thus a plurality of C-clips may be used as the connection members 251.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to various example embodiments, there may be provided a sensor module (e.g., the sensor module in FIG. 5) including: a circuit board (e.g., the circuit board 310 in FIG. 9); a biometric sensor (e.g., the biometric sensor 320 in FIG. 9) disposed in a first area (e.g., the first area A1 in FIGS. 10A and 10B) of a surface (e.g., the first surface 311 in FIGS. 10A and 10B) of the circuit board; a conductive line (e.g., the conductive line 313 in FIG. 9) disposed in a second area (e.g., the second area A2) of the first surface of the circuit board and surrounding at least a portion of the biometric sensor when viewed from above the first surface of the circuit board; a plurality of electrode pads disposed in a third area (e.g., the third area B1 in FIGS. 10A and 10B) of a second surface (e.g., the second surface 312 in FIGS. 10A and 10B) of the circuit board; and at least one electronic component comprising electronic circuitry (e.g., the electronic component 335 in FIG. 9) disposed in a third area of the second surface of the circuit board and electrically connected to the plurality of electrode pads.

According to various example embodiments, the sensor module may further include a shielding member (e.g., a shield) disposed in a fourth area (e.g., the fourth area B2 in FIGS. 10A and 10B) of the second surface of the circuit board, the shielding member being configured to protect the conductive line from noise outside the sensor module.

According to various example embodiments, the circuit board may include a plurality of stacked sub circuit board substrates (e.g., the plurality of sub circuit boards 310-1, 310-2, 310-3, and 310-4 in FIGS. 10A and 10B), and the conductive line (e.g., the conductive line 313-1, 313-2, 313-3, or 313-4 in FIGS. 10A and 10B) may be disposed on at least some of the plurality of sub circuit boards.

According to various example embodiments, at least one of the plurality of sub circuit boards includes a conductive plate (e.g., the conductive plate 315-1, 315-2, 315-3, or 315-4) disposed in the first area, and the conductive line is disposed to be spaced apart from the conductive plate by a predetermined distance.

According to various example embodiments, there may be provided a sensor module, in which the conductive line disposed on one sub circuit board among the plurality of sub circuit boards is electrically connected to the conductive line disposed on another sub circuit board stacked adjacent thereto, an input terminal and an output terminal of the conductive line of the one sub circuit board among the plurality of sub circuit boards are disposed at an inner side and an outer side of the one sub circuit board, respectively, and an input terminal and an output terminal of a conductive line disposed on another sub circuit board stacked adjacent to the one sub circuit board are disposed at an inner side and an outer side of the another sub circuit board, respectively.

According to various example embodiments, the circuit board may include: a first sub circuit board (e.g., the first sub circuit board 310-1 in FIGS. 10A and 10B) including a first conductive plate (e.g., the first conductive plate 315-1 in FIGS. 10A and 10B) disposed in a first area of the first sub circuit board and a first conductive line (e.g., the first conductive line 313-1 in FIGS. 10A and 10B) disposed in a second area of the first sub circuit board spaced apart from the first conductive plate by a predetermined distance; and a second sub circuit board (e.g., the second sub circuit board 310-2 in FIGS. 10A and 10B) stacked adjacent to the first circuit board, the second sub circuit board including a second conductive plate (e.g., the second conductive plate 315-2 in FIGS. 10A and 10B) disposed in a first area of the second sub circuit board and a second conductive line (e.g., the second conductive line 313-2 in FIGS. 10A and 10B) disposed in the second area of the second sub circuit board spaced apart from the second conductive plate by a predetermined distance.

According to various example embodiments, the size of the first sub circuit board and the size of the second sub circuit board are substantially equal to each other.

According to various example embodiments, a number of wound turns of the first conductive line and a number of wound turns of the second conductive line are substantially equal to each other.

According to various example embodiments, when the first sub circuit board is viewed from above, the input terminal of the first conductive line (e.g., the input terminal P1 of the first conductive line in FIGS. 10A and 10B) is disposed at a relatively inner side of the first sub circuit board compared to the output terminal of the first conductive line (e.g., the output terminal P2 of the first conductive line in FIGS. 10A and 10B), and when the second sub circuit board is viewed from above, the input terminal of the second conductive line (e.g., the input terminal P3 of the second conductive line in FIGS. 10A and 10B) is disposed at a relatively inner side of the second sub circuit board compared to the output terminal of the second conductive line (e.g., the output terminal P4 of the second conductive line in FIGS. 10A and 10B).

According to various example embodiments, the electronic components disposed on the another surface of the circuit board may include a processor configured to process or control at least some signals among biometric information signals acquired using the biometric sensor and wireless charging signals acquired using the conductive line.

According to various example embodiments, the sensor module may further include a protection member (e.g., the protection circuit members 314 and 337 in FIG. 9) disposed on at least one of the first surface and the second surface of the circuit board.

According to various example embodiments, the biometric sensor may include at least one light-emission member comprising light emitting circuitry (e.g., the light emission unit 321 in FIG. 9) configured to emit light and at least one light reception member comprising light receiving circuitry (e.g., the light reception members 322 and 323 in FIG. 9) spaced apart from the light emission unit and configured to receive reflected light corresponding to light emitted from the light emission unit and to convert the received light into a current signal.

According to various example embodiments, the biometric sensor may further include a wall (e.g., the wall 324 in FIGS. 10A and 10B) disposed between the light emission unit and the light reception member.

According to various example embodiments, the plurality of electrode pads may include at least one electrode pad (e.g., the electrode pad 330 in FIGS. 10A and 10B) electrically connected to the biometric sensor and at least one electrode pad (e.g., the electrode pad 334 in FIGS. 10A and 10B) electrically connected to the conductive line.

According to various example embodiments, the sensor module may generate a wireless charging signal using current generated in the conductive line by electromagnetic induction based on an external electronic device being located adjacent to the sensor module.

According to various example embodiments, there may be provided an electronic device (e.g., the electronic device 200 in FIG. 13) including: a housing (e.g., the housing 211 in FIG. 13) including a first surface (e.g., the first surface F in FIG. 13) oriented in a first direction (e.g., the first direction (Z-axis direction) in FIG. 13), and a second surface (e.g., the second surface R in FIG. 13) oriented in a second direction opposite the first direction; a display (e.g., the display 213 in FIG. 13) disposed such that at least a portion thereof is viewable through the first surface and configured to display information outwards; a main circuit board (e.g., the main circuit board 250 in FIG. 13) disposed in a space (e.g., the space S in FIG. 13) between the first surface and the second surface; a sensor module (e.g., the sensor module 300 in FIG. 9) disposed to be exposed to at least a partial area of the second surface; and a battery (e.g., the battery BAT in FIG. 13) disposed in a space between the first surface and the main circuit board. The sensor module may include: a circuit board (e.g., the circuit board 310 in FIG. 13) having one surface (e.g., the first surface 311 of the circuit board 310 in FIG. 13) facing the second surface of the housing and another surface (e.g., the second surface 312 of the circuit board 310 in FIG. 13) the facing the first surface of the housing; a biometric sensor (e.g., the biometric sensor 320 in FIG. 13) disposed in a first area (e.g., the first area A1 in FIGS. 10A and 10B) on the one surface of the circuit board; a conductive line (e.g., the conductive line 313 in FIG. 9) configured to wirelessly charge the battery, the conductive line being disposed in a second area (e.g., the second area A2 in FIGS. 10A and 10B) of the one surface of the circuit board and surrounding at least a portion of the biometric sensor when viewed from above the one surface of the circuit board; a plurality of electrode pads (e.g., the plurality of electrode pads 330 and 324 in FIGS. 10A and 10B) disposed in a third area (e.g., the third area B1 in FIGS. 10A and 10B) of the another surface of the circuit board; and an electronic component (e.g., the electronic component 335 in FIG. 13) disposed in the third area of the another surface of the circuit board and electrically connected to the plurality of electrode pads.

According to various example embodiments, the electronic device (e.g., the electronic device 200 in FIG. 13) may further include a shield (e.g., the shielding member 340 in FIG. 13) disposed in a fourth area (e.g., the fourth area B2 in FIGS. 10A and 10B) of the another surface of the circuit board, the shield being configured to protect the conductive line from noise outside the sensor module.

According to various example embodiments, the electronic device (e.g., the electronic device 200 in FIG. 13) may further include a connection member comprising a conductive material (e.g., the connection member 251 in FIG. 13) configured to electrically connect the main circuit board and the circuit board of the sensor module.

According to various example embodiments, in the electronic device (e.g., the electronic device 200 in FIG. 13), the circuit board may include a plurality of stacked sub circuit board substrates (e.g., the plurality of sub circuit boards 310-1, 310-2, 310-3, and 310-4 in FIGS. 10A and 10B), at least one of the plurality of sub circuit boards includes a conductive plate (e.g., the conductive plates 315-1, 315-2, 315-3, or 315-4 in FIGS. 10A and 10B) disposed in the first area, and the conductive lines (e.g., the conductive lines 313-1, 313-2, 313-3, or 313-4 in FIGS. 10A and 10B) disposed on at least some of the plurality of sub circuit boards are spaced apart from the conductive plate by a predetermined distance.

According to various example embodiments, in the electronic device (e.g., the electronic device 200 in FIG. 13), the conductive line disposed on one sub circuit board among the plurality of sub circuit boards may be electrically connected to the conductive line disposed on another sub circuit board stacked adjacent thereto, an input terminal and an output terminal of the conductive line formed on the one sub circuit board among the plurality of sub circuit boards may be disposed at an inner side and an outer side of the one sub circuit board, respectively, and an input terminal and an output terminal of a conductive line disposed on another sub circuit board stacked adjacent to the one sub circuit board may be disposed at an inner side and an outer side of the another sub circuit board, respectively.

While the electronic device of the disclosure has been illustrated and described with reference to the various example embodiments, it will be apparent to those skilled in the art that the electronic device is not limited to these embodiments and drawings, and various substitutions, modifications, and changes in form and details may be made thereto without departing from the spirit and scope of the disclosure, including the appended claims and their equivalents.

What is claimed is:

1. A sensor module comprising:
a circuit board;
a biometric sensor adjacent to a first area of a first surface of the circuit board;
an antenna comprising a conductive line for wireless charging disposed in a second area of the first surface of the circuit board and wound for at least one turn to surround at least a portion of the biometric sensor when viewed from above the first surface of the circuit board;
a plurality of electrode pads disposed in a third area of a second surface of the circuit board; and
at least one electronic component comprising electronic circuitry disposed in the third area and electrically connected to at least one of the plurality of electrode pads,
wherein the first surface and the second surface of the circuit board face in opposite directions,
wherein the sensor module further includes a shield disposed in a fourth area of the second surface of the circuit board,
wherein the circuit board includes a plurality of stacked sub circuit boards, and the antenna comprising the conductive line disposed on at least one of the plurality of stacked sub circuit boards, and
wherein the conductive line is wound by at least one turn around edges at least one of the plurality of stacked sub circuit boards.

2. The sensor module of claim 1, wherein at least one of the plurality of stacked sub circuit boards includes a conductive plate and a conductive line of the antenna which is spaced apart from the conductive plate by a predetermined distance.

3. The sensor module of claim 1, wherein a first conductive line of the antenna disposed on a first sub circuit board among the plurality of stacked sub circuit boards is electrically connected to a second conductive line of the antenna disposed on a second sub circuit board stacked adjacent thereto,
an input terminal and an output terminal of the first conductive line are disposed at an inner side and an outer side of the first sub circuit board, respectively, and
an input terminal and an output terminal of the second conductive line are disposed at an inner side and an outer side of the secondsub circuit board, respectively.

4. The sensor module of claim 1, wherein the circuit board includes:
a first sub circuit board including a first conductive plate disposed in a first area of the first sub circuit board and a first conductive line of the antenna disposed in a second area of the first sub circuit board spaced apart from the first conductive plate by a predetermined distance; and
a second sub circuit board stacked adjacent to the first sub circuit board, the second sub circuit board including a second conductive plate disposed in a first area of the second sub circuit board and a second conductive line of the antenna disposed in a second area of the second sub circuit board spaced apart from the second conductive plate by a predetermined distance.

5. The sensor module of claim 4, wherein a size the first sub circuit board is substantially equal to a size of the second sub circuit board.

6. The sensor module of claim 4, wherein a number of wound turns of the first conductive line is substantially equal to a number of wound turns of the second conductive line.

7. The sensor module of claim 4, wherein, when the first sub circuit board is viewed from above, an input terminal of the first conductive line is disposed at a relatively inner side of the first sub circuit board compared to an output terminal of the first conductive line, and
when the second sub circuit board is viewed from above, an input terminal of the second conductive line is disposed at a relatively inner side of the second sub circuit board compared to an output terminal of the second conductive line.

8. The sensor module of claim 1, wherein the at least one electronic component includes a processor configured to process or control at least some signals among biometric information signals acquired using the biometric sensor and wireless charging signals acquired using the antenna.

9. The sensor module of claim 1, further comprising:
a protection member comprising a protective material disposed on at least one of the first surface or the second surface of the circuit board.

10. The sensor module of claim 1, wherein the biometric sensor includes:
at least one light emitter configured to emit light; and
at least one light detector spaced apart from the light emitter, the light detector configured to detect reflected light corresponding to light emitted from the light emitter and to convert the detected light into a current signal.

11. The sensor module of claim 10, wherein the biometric sensor further includes a wall disposed between the light emitter and the light detector.

12. The sensor module of claim 1, wherein the plurality of electrode pads includes:
at least one electrode pad electrically connected to the biometric sensor; and
at least one electrode pad electrically connected to the conductive line.

13. The sensor module of claim 1, wherein the sensor module is configured to generate a wireless charging signal using current generated in the antenna by electromagnetic induction based on an external electronic device being located adjacent to the sensor module.

14. An electronic device comprising:
a housing including a first surface oriented in a first direction, and a second surface oriented in a second direction opposite the first direction;
a display disposed such that at least a portion thereof is viewable through the first surface;
a main circuit board disposed in a space between the first surface and the second surface;
a sensor module disposed to be exposed to at least a partial area of the second surface; and
a battery disposed in a space between the first surface and the main circuit board,
wherein the sensor module includes:
a circuit board having a first surface facing the second surface of the housing and second surface facing the first surface of the housing;
a biometric sensor disposed in a first area on the first surface of the circuit board;

an antenna for wirelessly charging the battery, the antenna comprising a conductive line disposed in a second area of the circuit board and wound for at least one turn to surround at least a portion of the biometric sensor when viewed from above the first surface of the circuit board;

a plurality of electrode pads disposed in a third area of the secondsurface of the circuit board;

an electronic component comprising electronic circuitry disposed in the third area and electrically connected to at least one of the plurality of electrode pads; and a shield disposed in a fourth area of the second surface of the circuit board, and wherein the circuit board includes a plurality of stacked sub circuit boards, and the antenna comprising the conductive line disposed on at least one of the plurality of stacked sub circuit boards, and wherein the conductive line is wound by at least one turn around edges of at least one of the plurality of stacked sub circuit boards.

15. The electronic device of claim 14, wherein the shield is configured to protect the conductive line from noise from outside the sensor module.

16. The electronic device of claim 14, further comprising:

a connector comprising a conductive material configured to electrically connect the main circuit board and the circuit board of the sensor module.

17. The electronic device of claim 14, at least one of the plurality of stacked sub circuit boards includes a conductive plate, and a conductive line of the antenna which is spaced apart from the conductive plate by a predetermined distance.

18. The electronic device of claim 17, wherein a first conductive line of the antenna disposed on a first sub circuit board among the plurality of stacked sub circuit boards is electrically connected to a second conductive line of the antenna disposed on a second sub circuit board stacked adjacent thereto, an input terminal and an output terminal of the first conductive line are disposed at an inner side and an outer side of the first sub circuit board, respectively, and an input terminal and an output terminal of the second conductive line are disposed at an inner side and an outer side of the second sub circuit board, respectively.

* * * * *